(12) United States Patent
Bystryak et al.

(10) Patent No.: US 8,951,722 B1
(45) Date of Patent: *Feb. 10, 2015

(54) METHODS FOR IMPROVING ANALYTE DETECTION USING PHOTOCHEMICAL REACTIONS

(71) Applicant: Allied Innovative Systems, LLC, Budd Lake, NJ (US)

(72) Inventors: Simon Bystryak, Budd Lake, NJ (US); Rasa Santockyte, Princeton, NJ (US)

(73) Assignee: Allied Innovative Systems LLC, Budd Lake, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/530,728

(22) Filed: Nov. 1, 2014

Related U.S. Application Data

(63) Continuation-in-part of application No. 14/071,287, filed on Nov. 4, 2013, now Pat. No. 8,916,341.

(51) Int. Cl.
| | | |
|---|---|---|
| *G01N 21/00* | (2006.01) | |
| *C12Q 1/00* | (2006.01) | |
| *G01N 33/533* | (2006.01) | |
| *C12Q 1/70* | (2006.01) | |
| *G01N 33/569* | (2006.01) | |
| *C12Q 1/28* | (2006.01) | |
| *C12Q 1/68* | (2006.01) | |
| *G01N 33/542* | (2006.01) | |

(52) U.S. Cl.
CPC .............. *G01N 33/533* (2013.01); *C12Q 1/703* (2013.01); *C12Q 2600/158* (2013.01); *G01N 33/542* (2013.01); *G01N 33/56911* (2013.01); *G01N 33/56983* (2013.01); *G01N 33/56988* (2013.01); *G01N 33/56994* (2013.01); *G01N 33/569* (2013.01); *C12Q 1/28* (2013.01); *C12Q 1/682* (2013.01); *Y10S 436/905* (2013.01)
USPC .............................................. 435/4; 436/905

(58) Field of Classification Search
None
See application file for complete search history.

(56) References Cited

U.S. PATENT DOCUMENTS

| 5,776,703 A | 7/1998 | Bystryak |
| 8,916,341 B1 * | 12/2014 | Bystryak et al. ................. 436/5 |
| 2002/0110842 A1 | 8/2002 | Bystryak |

OTHER PUBLICATIONS

Bystryak and Mekler. Photochemical amplification for horseradish peroxidase-mediated immunosorbent assay. Anal. Biochem. 1992; 202(2): 390-393.*
Moore DE: Antioxidant efficiency of polyhydric phenols in photooxidation of benzaldehyde. J Pharm Sci. 1976;65:1447-51.

* cited by examiner

*Primary Examiner* — Zachariah Lucas
*Assistant Examiner* — Stuart W Snyder
(74) *Attorney, Agent, or Firm* — Boris Leschinsky

(57) ABSTRACT

An improved assay for detecting an analyte in a fluid sample includes a step of conducting a photochemical reaction, in which a substrate conversion catalyzed by a photosensitizer into a product of the photochemical reaction is temporary inhibited when the reaction mixture is irradiated with a light at a wavelength within a light absorption spectrum of the photosensitizer. The photosensitizer (or an enzyme to catalyze producing thereof) is attached to an entity having an affinity to the analyte, such entity is bound to the analyte prior to irradiation. To achieve temporary inhibition, certain additives are used such as ascorbic acid or its derivatives. The assay may increase the sensitivity of ELISA 20- to 100-fold.

14 Claims, 15 Drawing Sheets

| Samples | 10 min illumination | 15 min illumination | 20 min illumination | Mean | CV, % |
|---|---|---|---|---|---|
| Low positive | 2,440.21 | 2,419.97 | 2,371.52 | 2,410.57 | 1.46 |
| PS 1:200 | 32,086.65 | 35,701.64 | 37,651.38 | 35,146.56 | 8.03 |
| TJS 1:400 | 15,878.27 | 16,059.48 | 16,499.46 | 16,145.73 | 1.98 |
| CAP-5-05 1:100 | 19,044.16 | 20,842.84 | 21,107.97 | 20,331.66 | 5.52 |

Figure 7D

| | Conventional method, original protocol | | Conventional method, modified protocol | | Photoamplification method, modified protocol | |
|---|---|---|---|---|---|---|
| Samples | Mean | CV, % | Mean | CV, % | Mean | CV, % |
| Low positive | 3,608 | 50.70 | 2,536 | 41.09 | 3,391 | 52.83 |
| PS | 42,028 | 39.68 | 39,897 | 35.93 | 38,361 | 11.27 |
| TJS | 28,527 | 47.16 | 22,491 | 25.14 | 15,230 | 8.50 |
| CAP-5-05 | 17,363 | | 17,363 | | 18,665 | |

METHODS FOR IMPROVING ANALYTE DETECTION USING PHOTOCHEMICAL REACTIONS

CROSS-REFERENCE DATA

This is a continuation-in-part of the co-pending U.S. patent application Ser. No. 14/071,287 filed Nov. 4, 2013 with the same title, incorporated herein by reference in its entirety.

REFERENCE TO GOVERNMENT SPONSORED RESEARCH

This invention was made with government support in the form of a grant No. AI055310 entitled "A new PCR-based method for HIV detection" and a grant No. AI083169 entitled "Ultrasensitive method for HIV p24 antigen detection", both grants were awarded by the National Institute of Allergy and Infectious Diseases (NIAID), National Institutes of Health (NIH). The Government has certain rights in this invention.

BACKGROUND OF THE INVENTION

This invention relates to methods for improving detection of various physiologically active substances in tested fluids Immunoassays, hybridization, ligand-receptor and enzymatic assays are widely used in biology and medicine for detection of viruses, bacteria, cancer markers, and for drug screening (Edberg, 1985; Catty, 1989).

In particular, immunoassay and hybridization assays are used for detection of a number of pathogenic bacteria and viruses that can be considered possible biological warfare agents. Among them are an Anthrax (*Bacillus anthracis*), an Arenaviruse, a *Clostridium botulinum* toxin, a *Brucella* specie, a *Burkholderia pseudomallei*, a *Chlamydia psittaci*, a *Vibrio cholerae*, an Ebola virus, a variola major, a Staphylococcal enterotoxin B, a *Francisella tularensis*, a *Rickettsia prowazekii*, a *Yersinia pestis*, a *Cryptosporidium parvum*, and food- and water-borne bacteria, such as *Salmonella* sp., an *Escherichia coli* O157:H7, *Shigella*, *Staphylococcus aureus*, *Campylobacter jejuni*, *Campylobacter coli*, *Listeria. monocytogenes* and *Bacillus cereus*. They are included in bioterrorism pathogens list published by the Centers of Disease Control and Prevention (CDC). These agents are considered possible biological warfare agents because they are resistant to environmental conditions, most of the human population is completely susceptible, and the diseases some of them cause are severe with a high fatality rate. A large quantity of these organisms could easily be grown and preserved for several years. These agents are also environmental and food chain-safety threats.

The effective testing of, for instance, pathogenic bacteria requires methods of analysis that meet a number of challenging criteria. Time and sensitivity of analysis are the most important limitations related to the usefulness of microbiological testing. Bacterial detection methods have to be rapid and very sensitive since the presence of even a single pathogenic organism in the water, body or food may be an infectious dose. At present, three groups of tests for food- and water-borne bacteria are, mainly, used: 1) culture methods, 2) immunoassay, and 3) polymerase chain reaction (PCR)-based assays. Culture methods are laborious, time-consuming and very expensive. They require a minimum of several days to perform. Polymerase chain reaction (PCR) method is based on amplification of small quantities of genetic material to determine the presence of bacteria. The PCR method is rather sensitive, but requires pure samples and hours of processing and expertise in molecular biology (Meng et al., 1996; Sperveslage et al., 1996). Immunoassay methods, which yield a presumptive positive or negative screening result in 24 h or less have also been developed. Typical sensitivities of immunoassays are approximately $10^6$ CFU/ml, although more sensitive variants of immunoassay (with sensitivities of $10^2$-$10^5$ CFU/ml) are being developed (Yu and Bruno, 1996; Mazenko et al., 1999).

Thus, there is a need in highly sensitive, rapid and reliable analytical methods for detection of water- and food-borne pathogens. In response to this problem, considerable effort is now directed towards the development of methods that can rapidly detect low concentrations of pathogens in water, food and clinical samples. For this purpose, a number of instruments are being developed using various principles of detection, e.g. chromatography, infrared or fluorescence spectroscopy, bioluminescence, flow cytometry, impedimetry and many others (Ivnitski et al., 1999). Despite these efforts, the only a few biosensors for bacterial detection are commercially available or are approaching commercialization. The main reasons for this are the challenges to create biosensors with the necessary sensitivity and properties for reliable and effective use in routine applications. Since the present invention allows one to increase the sensitivity of the analytical biochemical methods significantly, it has a paramount value for a more reliable detection of potential biological warfare agents.

Very sensitive analytical biochemical methods are also of significant value for detection of infectious diseases. For example, in spite of using sensitive Enzyme-linked immunosorbent assays (ELISA) for the detection of HIV, Hepatits B and C viruses in blood donors, the residual risk of post-transfusion infection remains. The enzyme immunoassay testing currently used for HIV and Hepatitis B testing produces many false negative results. For example, deaths due to fulminant post-transfusion hepatitis B have been reported although HBsAg-negative blood on ELISA was transfused (Arababadi et al., 2011). The amount of HBsAg contained in the peripheral blood of these HBsAg-negative HBV carriers is so small that the currently employed methods are inadequate (Sawke and Sawke, 2010).

Other physiologically active substances that require high sensitivity methods to be detected are pathogenic bacteria, viruses, cancer biomarkers such as *Clostridium difficile* toxin A, a *Clostridium difficile* toxin B, a rotavirus, a p50 recombinant protein NFkB p50 homodimer, an RNA, a DNA, an mRNA, an cDNA, and a prostatic specific antigen (PSA).

Formats of Analytical Biochemical Assays

There are a number of various formats of immuno- and hybridization assay and ligand-receptor assays that are used in clinical and research practice. They are based on the use of either antigen-antibody, ligand-receptor or oligonucleotides hybridization reactions for detection of the analyte to be detected, and use of labels (markers) of different origin: photochemical, radioactive, enzymatic, fluorescent, chemiluminescent and others.

1. Assays Based on the Use of Photochemical Labels

It has been reported that certain dyes, for instance derivatives of fluorescein, rhodamine, erythrosine, eosin, methylene blue, Bengal rose, porphyrin, phthalocyanine and many others were used as photochemical labels in various analytical biochemical assays. These dyes possess a high yield to their triplet state, and therefore, can be used as photosensitizers (photocatalysts) of the photochemical reactions. Under certain conditions photochemical reaction between such dye and selected substrate occurs and takes place only under irradiation with certain range of light wavelengths.

Photochemical Reactions and Photooxidation.

Chemical reactions caused by absorption of light are defined as photochemical reactions. Photoexcitation is the first step in a photochemical process in which the photon can be absorbed directly by the reactant or by a photosensitizer which absorbs the photon and transfers the energy to the reactant. There are several types of photochemical reactions. One such type is photosensitized oxidation implicated in numerous processes in vivo and in vitro. Many of these oxidation processes can occur in the dark; however, light can accelerate oxidation due to the photochemical generation of free radicals (type I photosensitized oxidation) or singlet oxygen (type II photosensitized oxidation). Strongly light-absorbing organic dye molecules such as Rose Bengal, erythrosine, eosin, methylene blue, porphyrines and phthalocyanines are typical examples of photosensitizers that can participate in Types I and II photochemical reactions. In Type II photochemical reaction, produced singlet oxygen reacts with many organic compounds including aromatics, vitamins, steroids, fatty acids, aminoacids, proteins, nucleic acids, and synthetic polymers (Timoshenko, 2009). Photosensitized oxidation involving singlet oxygen is implicated in analytical assays, phototherapy of cancer, photocarcinogenesis, photodynamic inactivation of viruses and cells, and in photodegradation of organic compounds (Schmidt, 2006b; Schmidt, 2006a).

Various formats of analytical assays using photosensitizers as labels for determination of physiologically active substances (analytes) have been described in patent and scientific literature. In references (Motsenbocker et al., 1993a; Motsenbocker et al., 1993b) derivatives of methylene blue were used as labels in Enzyme-Linked Immunosorbent Assay (ELISA)-type assays. In this assay, a methylene blue dye derivative was synthesized and covalently attached to detection antibody. Upon irradiation of the solution containing luminol by pulsed red light, a photosensitive dye is excited and plays a role of photosensitizer (photocatalyst) of luminol oxidation which results in generation of blue light. An alpha-fetoprotein immunoassay based on this principle was developed having a detection limit of 17 pg.

It has also been reported that fluorescein, rodamine and eosin can be utilized as photochemical antibody labels in immunohistochemistry. It was shown that DAB can be photooxidized by these dyes in immunolabeled cultured cells (Sandell and Masland, 1988). In this case, the fluorochrome which is a label for the antibody bound to the cell, is utilized as a photosensitizer in the photochemical reaction of DAB oxidation. Since the production of reactive oxygen species by the fluorophore has been implicated in the photooxidation reaction (Sandell and Masland, 1988), the experiment made use of test fluorescent compounds that were more potent generators of singlet oxygen. Many of the compounds currently used for immunofluorescent and tyramine-based labeling, such as fluorescein and rhodamine were chosen because of their high fluorescence quantum yields, and have comparatively low yields of singlet oxygen ($^1O_2$). Eosin, a brominated derivative of fluorescein, has a singlet oxygen quantum yield (0.57) approximately 19 times greater than fluorescein (Gandin et al., 1983), while still possessing moderate fluorescence (~20% as bright as fluorescein) (Fleming et al., 1977). Other fluorescein derivatives such as erythrosine and Rose Bengal are also known to be effective photosensitizers and singlet oxygen generators, and can be used as labels in immunohistochemistry.

Two homogeneous (not requiring physical separation of labeled and unlabeled reagents) immunoassay techniques based on the use of photogeneration of singlet oxygen have been independently developed. The first method is based on (a) photooxidation by singlet oxygen ($^1O_2$) of a fluorescent substrate (1,3-diphenylisobenzofuran, DPBF) embedded in unilamellar vesicles on the surface of which antibody to the analyte antigen is covalently attached (DPBF-immunoliposomes); (b) generation of singlet oxygen, upon illumination, by a chromophore (erythrosine) covalently attached to an antibody (Ab*) or antigen (Ag*); (c) formation of a "sandwich"- or "competition"-type complex whereupon the singlet oxygen-generating chromophore conjugate (Ab* or Ag*) and immunoliposome-embedded DPBF are brought into close proximity (Bystryak et al., 1995; Bystryak, 1998). Competition- and sandwich-type model assay systems for the detection of protein antigens and viruses were developed.

In the second method, the Luminescent Oxygen Channeling Immunoassay (LOCI) (Ullman et al., 1994), singlet oxygen is generated by a photosensitizer and an antenna dye that are dissolved in one of the particles. Singlet oxygen molecule diffuses to the second particle and initiates a chemiluminescent reaction of an olefin that is dissolved in it. The technique permits real-time measurement of particle binding kinetics when analyte is present in the solution. By using antibody-coated particles, a homogeneous immunoassay capable of detecting approximate to 4 amol of thyroid-stimulating hormone in 12 min was demonstrated.

AlphaScreen/AlphaLISA assays developed based upon an oxygen channeling technology, LOCI are bead based proximity assays when the donor, which contains phthalocyanine, is laser excited and ambient oxygen is converted to singlet oxygen. This is a highly amplified reaction since approximately 60,000 singlet oxygen molecules can be generated and travel at least 200 nm in aqueous solution before decay. Consequently, if the Donor and Acceptor beads are within that proximity, energy transfer occurs. Singlet oxygen reacts with chemicals (substrates) in the Acceptor beads to produce a luminescent response (Eglen et al., 2008). AlphaScreen/AlphaLISA assays are immunoassays as well as high throughput drug screening assays involving antigen-antibody, oligonucleotide hybridization, biotin-streptavidin, ligand-receptor binding reactions and enzymatic reactions.

2. Assays Using Enzymes as Labels

Since the introduction, in 1966, of enzymes as markers for the labeling of antigens and antibodies (Avrameas and Uriel, 1966; Nakane and Pierce, 1966), immunoenzymatic techniques have been considerably developed and diversified. These techniques are now routinely used for detection of physiologically active substances in body fluids, localization of antigens or antibodies on tissues, detection of antigens or antibodies immobilized on various solid phases, as well as for the titration of antibodies, and for the precise measurement of antigens. Antigens and/or antibodies are localized, detected and/or titrated by means of various heterogeneous procedures.

In general, heterogeneous immunoenzymatic procedures are based on the use and detection of enzyme-antibody or enzyme-antigen conjugates, prepared according to several established protocols. Sometimes, antibody or antigen is coupled to enzyme through biotin-streptavidin bond, which is antibody (or antigen)-biotin-streptavidin-enzyme conjugate is used. The enzyme is detected using chromogenic, fluorogenic or chemiluminescent enzyme substrates by detecting a corresponding signal obtained from the product of the enzymatic reaction.

For example, in conventional Enzyme Linked Immuno-Sorbent Assay (ELISA), antibody against analyte to be detected is attached to solid phase, particularly, polystyrene microtiter plate. Then, body fluid with unknown concentration of the analyte and enzyme-labeled antibody to analyte are added. This results in formation of antibody-analyte-enzyme-labeled antibody complex on the surface of the solid phase. After incubation, the unbound analyte and enzyme-labeled antibody is removed from the solution by rinsing. Then, a substrate solution is added to the test tube or well, and the amount of the bound enzyme-conjugated antibody and, consequently, the concentration of the analyte is determined by detecting color, fluorescence or luminescence signals of the liquid phase in the final reaction mixture.

Other than ELISA methods that use enzyme as a label include hybridization assays, Immunohistochemistry (IHC) and in situ hybridization (ISH) assays, blotting analysis, immunochromatography and other methods. Hybridization and in situ hybridization (ISH) assays are based on oligonucleotides binding whereas Immunohistochemistry (IHC), blotting analysis and immunochromatography methods are based on antigen-antibody reactions in the same way as ELISA.

However, in many cases, the sensitivity of these assays is inadequate. Therefore, there is a need in development of more sensitive assays. In order to detect constituents (analytes) present in small amounts, it is necessary to devise procedures capable of strongly amplifying the signal and/or increasing of signal-to-noise ratio, which results in increasing of the analytical sensitivity of the assay. Since all heterogeneous immunoenzymatic techniques involve, in their final step, the detection of an enzyme associated with solid phase, essentially two approaches have been developed to obtain such enzymatic signal amplification. The first includes procedures leading to a high accumulation of enzyme labels associated with the solid phase. The second consists of procedures that make use of enzyme substrate derivatives, which give rise to reaction products detectable in minute amounts. The present invention relates to the second approach, which is also applicable to some assays using photosensitized photochemical reactions.

A type of amplification technique that can be employed for enzyme-mediated assays utilizes light or photonic energy to increase the sensitivity of the assay. This technique is disclosed in U.S. Pat. No. 5,776,703. It is widely known that some chemical reactions are photosensitive dependent upon the quantum chemical structure and other properties of the reactants. The rate of a photosensitive reaction is much higher if the reaction mixture is illuminated by an intense light of a specific wavelength compared to a similar reaction taking place in the absence of such light.

The technique described in the '703 patent includes the binding of an antibody to a suspected antigen, wherein the antibody is labeled with an enzyme such as HRP and added to a biological liquid, for example blood or serum. A portion of the HRP-labeled antibodies binds with the antibodies that are specific to the antigen and existing already in the biological liquid to form an [antibody]-[antigen]-[HRP labeled antibody] complex. Subsequently, after an incubation time, the HRP-labeled antibody which did not bind to the Ab-Ag complex is removed from the solution by rinsing or washing. Then, a substrate solution containing $H_2O_2$ and OPD (ortho-phenylenediamine) is added to the test tube and the OPD is oxidized with HRP acting as an oxidizing catalyst. The oxidation product of HRP-catalyzed reaction of OPD oxidation is diaminophenazine (DAP). DAP is a colored substance, and the optical density of the solution containing DAP can be read with the aid of a spectrophotometer or microplate reader. At this point in the assay a stopping solution, such as sulfuric acid, is used in order to stop the various chemical reactions from proceeding and producing reaction products that may interfere with an accurate measurement. The final signal is proportional to the concentration of HRP bound to antibodies and therefore to the added antibodies forming the Ab-Ag-(Ab-HRP) complex.

The '703 patent further discloses that the procedure performed to this point can be enhanced by the application of intense light at the wavelength of 400 to 500 nm before adding a stop solution containing acid. Prior to a spectrophotometer (or fluorometer) reading, the test tube is illuminated by an intense source of light of a wavelength in the above range. The DAP obtained in the first stage of the reaction is a photosensitizer for the following photochemical reaction of OPD oxidation, and together with the light photons serve as new catalyzing agents for further production of DAP. Thus a two stage process takes place:

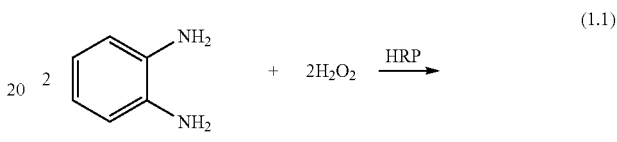

OPD (uncolored)

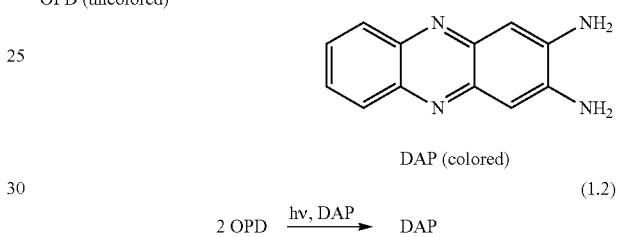

DAP (colored)

$$2\ OPD \xrightarrow{h\nu,\ DAP} DAP \quad (1.2)$$

The resulting optical density or fluorescence of the sample is measured by a spectrophotometer or fluorometer, respectively, and the results obtained by the '703 patent are an improvement over the prior art. However, this method suffers from the limited sensitivity due to the fact that both useful and background (noise) signals increase within a photochemical step (1.2). This severely restricts the utility of the method. It should be emphasized that other binding agents and pairs such as oligonucleotides, oligonucleotide-protein, biotin-avidin(streptavidin) and protein-protein can be used in such kind of assays.

An attempt of modification of the technique disclosed in U.S. Pat. No. 5,776,703 was done in US PATENT APPLICATION PUBLICATION No. 2002/0110842, which is incorporated herein by reference in its entirety. The '842 application describes adding of some detergents to the OPD substrate solution to increase the sensitivity of the assay including a photochemical amplification step. The best mode of practicing the '842 invention included the commercially available detergent Triton X-100 as an additive at a concentration in the range of 10% in a phosphate/citrate buffer with a pH of approximately 5.0. Triton X-100 has a chemical formula of $C_{14}H_{22}O(C_2H_4O)n$, where the average number of ethylene oxide units per molecule, n, ranges from 9 to 10.

Also disclosed is the use of Tween-20, another commercially available detergent, as an additive. However, the addition of detergents to the OPD substrate solution results in increase of the rate of the photochemical reaction (1.2) only; the sensitivity of the method was not improved as compared to the method described in the '703 patent.

Although the methods described in '703 patent and '842 application have increased the sensitivities of assays versus prior art methods, it is still desirable to have an even more sensitive technique. In addition to sensitivity, it would be beneficial to have an immunoassay method that further improved the signal-to-noise (S/N) ratio, which would substantially increase the effective range of the known methods. The methods of the '703 patent and the '842 application are adversely affected to a large degree by background noise. In addition, these methods are highly dependent upon a number of factors including: (1) the wavelength of the light used to catalyze the reaction; (2) the intensity of the light (the number of photons used to catalyze the reaction); and, (3) the illumination exposure (intensity x time).

It is therefore desirable to have an assay of detecting an analyte in a sample with increased sensitivity compared to known assays. It is also desirable to have an assay for detecting an analyte in a sample with an improved S/N ratio compared to known assays. It is also desirable to have an assay for detecting an analyte in a sample that can be used with existing ELISA and other assays methodology.

SUMMARY OF THE INVENTION

A photochemical method of the present invention (PMI) includes carrying out an analytical assay for detection of the analyte and utilizing photochemical reactions in which certain additives are used to increase the signal-to-noise ratio, sensitivity and rate of the analytical assay. The assay may be commercialized as a kit comprising novel solutions of the additives, the addition of which results in increased sensitivity of the conventional testing methods and/or rates of the photochemical reaction.

It is therefore an object of the invention to provide an assay for detecting an analyte in a sample, wherein the assay utilizes a photochemical reaction. The addition of the reagents described in this invention has increased sensitivity compared to known conventional assays and other methods utilizing photochemical reaction.

It is another object of the invention to provide an improved assay for detecting an analyte in a sample with an improved signal-to-noise ratio (S/N ratio) and sensitivity as compared to known assays utilizing photochemical reactions.

These and other objects are obtained by providing an assay for the determination of an analyte in a fluid sample comprising a step of conducting a photochemical reaction, in which a substrate conversion is catalyzed by a photosensitizer into a product of the photochemical reaction. This reaction is temporary inhibited when the reaction mixture is irradiated with a light at a wavelength within a light absorption spectrum of the photosensitizer. The photosensitizer or an enzyme to catalyze producing of the photosensitizer is attached to an entity having an affinity to the analyte. The entity is bound to the analyte prior to irradiation with the light.

It is yet another object of the invention to provide an improved assay for detecting an analyte in a sample, which may be compatible with existing ELISA methodology.

Yet another object of this invention is to provide improved assays to detect HIV p24 antigen, Hepatitis B and C antigens and antibodies, prostate specific antigen, *E. coli* and *Listeria* bacteria and other possible biological warfare agents and other physiologically active compounds and analytes.

The method of the invention includes the steps of binding to the analyte of an entity having an affinity to the analyte. This entity may be labeled with a photosensitizer or an enzyme to catalyze producing of the photosensitizer. Some additive or additives such as ascorbic acid or its certain derivatives may be added to the solution before performing the following photochemical reaction. Thus, the sample is irradiated with photonic energy, whereby the additives and the photonic energy provide catalysis for further production of the products of the photochemical reaction. The absorbance (OD), fluorescence, chemiluminescence or electrochemical parameters of the product of the photochemical reaction may be then measured to determine the concentration of this product, and, thereby, the analyte concentration in the fluid may be determined.

BRIEF DESCRIPTION OF THE FIGURES

FIG. 1A shows calibration curves obtained at various times of illumination for detection of the DAP primer added to the OPD substrate solution in the absence of the reagent solution (no additives);

FIG. 1B shows kinetics of the DAP-mediated reaction of OPD oxidation in the absence and presence of the reagent solution containing 250 μM ascorbic acid;

FIG. 1C shows calibration curves obtained at various times of illumination for detection of the DAP primer added to the OPD substrate solution in the presence of the reagent solution containing 250 μM ascorbic acid;

FIG. 1D shows calibration curves obtained at various times of illumination for detection of the DAP primer added to the OPD substrate solution in the presence of the reagent solution containing 500 μM ascorbic acid and 1.5% Tween 20.

FIGS. 7A through 7E show determination of HIV-1 viral load using AMPLICOR HIV MONITOR Test, version.1.5 (Roche)+PMI using less powerful illumination device as follows:

FIG. 7A shows dependences of ODs for low positive control (at starting dilution 1:64) on dilution factor at various times of illumination;

FIG. 7B shows dependences of ODs for Quantitation standard (at starting dilution 1:5) on dilution factor at various times of illumination;

FIG. 7C shows the signals (ODs) obtained for sample PS at starting dilution 1:200 and Quantitation Standard at dilutions 1:10 and 1:50 at different times of illumination as a function of a dilution factor;

FIG. 7D shows HIV-1 loads calculated using a modified protocol; and

FIG. 7E shows the average HIV-1 loads calculated using original and modified protocols.

FIGS. 8A through 8C show using of OPD as an insoluble HRP substrate in membrane- and cell-based assay as follows:

FIG. 8A shows a comparison of HRP substrates: Signals obtained for HRP-conjugated antibody spotted on nitrocellulose membrane (GE Healthcare) at decreasing concentrations (dilutions of its stock solution are shown on the right) and immersed into the indicated substrate solutions;

FIG. 8B shows the signals obtained for HRP-conjugated antibody spotted on nitrocellulose (strips 1 and 3) and Nylon membranes (strips 2 and 4) without blocking (strips 1 and 2) and with blocking for 2 hours at room temperature (strips 3 and 4) and immersed into OPD substrate solution; and FIG. 8C shows signals obtained for HRP-conjugated antibody spotted on Nylon membrane at decreasing concentrations (dilutions of its stock solution are shown on the right) without (strip 1, TMB and strip 2, OPD) and with PMI (OPD and the reagent solution containing 250 μM ascorbic acid 1.5% Tween 20).

DEFINITIONS

Figure 1A:
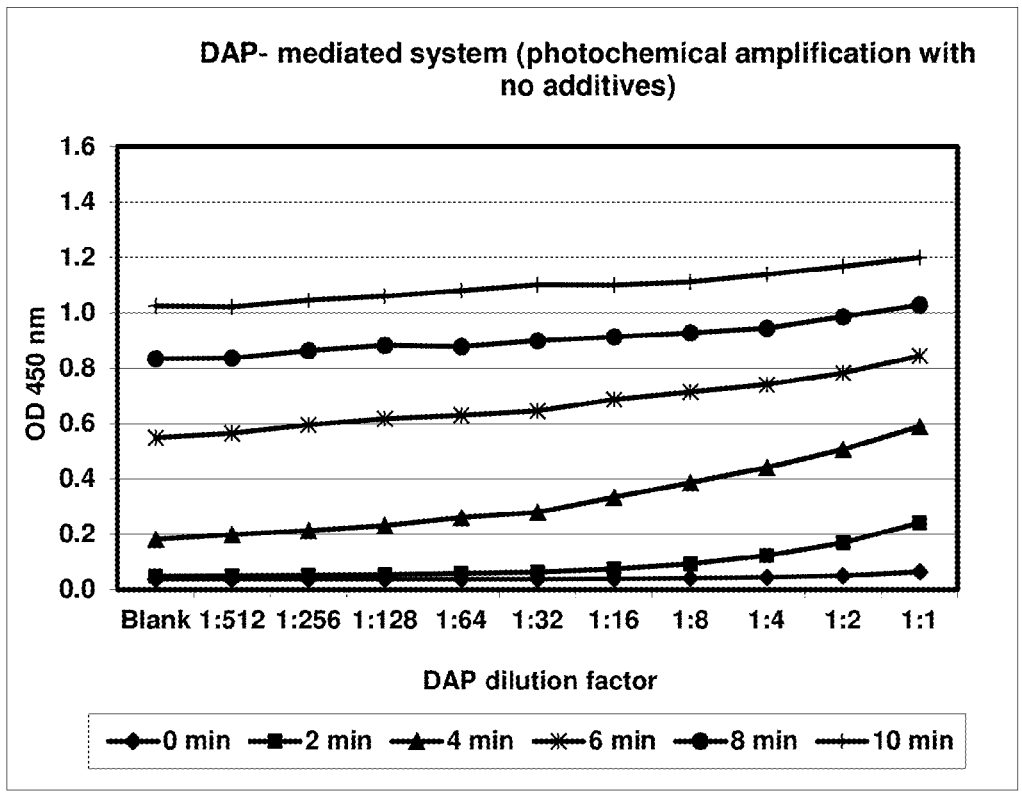
FIGS. 1A through 1D describe effect of various additives contained in reagent solutions on the calibration curves and kinetics of DAP-mediated photochemical reaction of OPD oxidation as follows.

"Reagent solution" or "Inhibitors" or "Retarders" means a solution or other physical form (solid, liquid, suspension, tablet) comprising one or more novel additives described in this disclosure: antioxidants, alcohols, detergents (surfactants), sugars, polymers, organic and inorganic reducers, and scavengers of reactive oxygen species (ROS).

"Antioxidant" means a molecule capable of slowing or preventing the oxidation of other molecules. Non-limiting examples of antioxidants include ascorbic and iso-ascorbic acids and their derivatives (such ascorbates and iso-ascorbates, ascorbic acid palmitate, stearate, and the like), tocopherols and trienols (alpha-, beta-, gamma- and delta-tocopherols and trienols), their derivatives and synthetic soluble tocopherol analogs similar to Trolox, flavanoids (myricetin, quercetin, rutin, kaempferol, and the like), antioxidant phenolic compounds other than flavanoids (BHA, BHT, TBHQ, riboflavin, tert-butyl phenol, gallic acid, caffeic acid, and similar), thiols and hydrosulfites (mercaptoethanol, L-cystein, dithiothreitol, dithionite, dithioerythritol and the like), carotenoids (xanthopylls and carotenes), melatonin, uric acid and derivatives, ubiquinones and quinones, lactates, NADH and its analogs, calcium antagonists, vitamin B6, aspirin, steroids pyrrolopyrimidines, ebselen, metallothioneins, metalloporphyrins, fullerenes and antioxidant mixtures.

"Alcohol" means a compound of the formula $C_nH_{2n+1}(OH)_x$, wherein $n>/=2$, $x=/>1$. Examples include but are not limited to methanol, ethanol, glycerol and ethyleneglycol (HO—CH$_2$—CH$_2$—OH) and their polymer analogs.

"Surfactant" means a substance that lowers the surface tension of a liquid. They may be ionic or non ionic. Non-limiting examples of surfactants include:

"Ionic surfactant" may include the following by way of an example:
1. Anionic (based on sulfate, sulfonate or carboxylate anions)
   a) Perfluorooctanoate (PFOA or PFO)
   b) Perfluorooctanesulfonate (PFOS)
   c) Sodium dodecyl sulfate (SDS), ammonium lauryl sulfate, and other alkyl sulfate salts
   d) Sodium laureth sulfate, also known as sodium lauryl ether sulfate (SLES)
   e) Alkyl benzene sulfonate
   f) Soaps, or fatty acid salts
2. Cationic (based on quaternary ammonium cations)
   a) Cetyl trimethylammonium bromide (CTAB) a.k.a. hexadecyl trimethyl ammonium bromide, and other alkyltrimethylammonium salts
   b) Cetylpyridinium chloride (CPC)
   c) Polyethoxylated tallow amine (POEA)
   d) Benzalkonium chloride (BAC)
   e) Benzethonium chloride (BZT)
3. Zwitterionic (amphoteric)
   a) Dodecyl betaine
   b) Cocamidopropyl betaine
   c) Coco ampho glycinate "Nonionic surfactant" may include the following by way of an example:
1. Alkyl poly(ethylene oxide)
2. Alkylphenol poly(ethylene oxide)
3. Copolymers of poly(ethylene oxide) and poly(propylene oxide) (commercially called Poloxamers or Poloxamines)
4. Alkyl polyglucosides, including:
   a) Octyl glucoside
   b) Decyl maltoside
5. Fatty alcohols
   a) Cetyl alcohol
   b) Oleyl alcohol
6. Cocamide MEA, cocamide DEA
7. Polysorbates: Tween 20, Tween 80
   a) Dodecyl dimethylamine oxide "Sugar" include the following examples: monosacharides (erythrose, arabinose, ribose, glucose, mannose, xylose, fructose, galactose, and the like), disaccharides (sucrose, maltose, cellobiose, lactose, and the like), oligosaccharides (raffinose, stachyose, cyclodextrins, and the like).

Non-limiting examples of "polymers" include polysaccharides (amylose, amylopectins, glycogen, cellulose, their derivatives, and the like), and polyethylene glycols.

"Scavengers of reactive oxygen species (ROS)" include but are not limited to non-enzymatic scavengers such as antioxidants with high-reducing potentials and enzymatic scavengers such as superoxide dismutase (SOD), superoxide reductases, catalase, thioredoxin reductase, alkenal/one oxidoreductase, and peroxiredoxins.

"PA" or "PAM" refers to Photo Amplification or Photoamplification Methods disclosed in U.S. Pat. No. 5,776,703 and US patent application publication No. 2002/0110842.

"PMI" refers to the Photochemical Method of the present Invention.

DETAILED DESCRIPTION OF THE INVENTION

An improved assay of the present invention for detecting an analyte in a fluid sample comprises a step of binding an entity labeled with a photosensitizer (or an enzyme to catalyze producing a photosensitizer) to the analyte. A critical step of the process is adding a reagent solution with an additive to cause a temporary inhibition of a conversion of a substrate added to a mixture of the entity and the analyte into a product of a photochemical reaction. Once the additive is depleted, this conversion is accelerated while a mixture of the entity, the analyte and the substrate is irradiated with a light at a wavelength within a light absorption spectrum of the photosensitizer.

In embodiments, the assay of the invention may be conducted by following these steps:
a) binding the analyte to a first entity having an affinity to the analyte, this entity labeled with a photosensitizer or an enzyme to catalyze producing of the photosensitizer,
b) adding to a mixture of the analyte and the entity a substrate for a photochemical reaction, which substrate is capable to be converted to a product of the photochemical reaction when the mixture of the entity, the analyte and the substrate is irradiated with a light at a wavelength within a light absorption spectrum of the photosensitizer,
c) adding a reagent solution containing an additive described by formula (1)

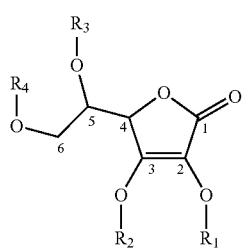

(1)

wherein the additive is an ascorbic acid or a derivative thereof obtained by at least one substitution at position 2, position 3, position 5, position 6 or any combinations thereof with at least one group of atoms selected from a group consisting of an anion group of atoms, an aliphatic group of atoms not exceeding 16 carbon atoms, and an aromatic group of atoms not exceeding 16 carbon atoms;
d) conducting the photochemical reaction by irradiating the mixture of step (c) with the light, and
e) detecting the analyte by measuring an optical signal corresponding to the amount of the product of the photochemical reaction.

In embodiments, the entity having an affinity to the analyte may be an antibody, an antigen, a ligand or a receptor. Dyes may be attached as a label to such entity. Certain dyes, for instance derivatives of fluorescein and rhodamine may be used as labels or markers of antibodies and antigens. In one embodiment of the invention, the photosensitized materials used as labels may include dyes with a significant yield to their excited triplet state. Exemplary dyes may include derivatives of phenazine, fluorescein, eosin, erythrosine, phthalocyanine, porphyrin, aminolevulinic acid, chlorine, purpurin, methylene blue, and Bengal rose.

In embodiments, a photochemical reaction between such dye and a substrate may take place only under irradiation with light of defined wavelength. The products of such photosensitized reactions may be colored, fluorescent, chemiluminescent or electrochemical materials which may be detected and measured using such known instruments and spectrophotometer (optical density reader), fluorometer, chemiluminometer or tools to measure electrical current parameters, respectively.

The principal difference (and advantage) of the assay of the present invention as compared to other known photochemical diagnostic procedures is the use of additives to the substrate solution to temporary inhibit the photochemical reaction—until such additives are depleted. Use of such additives leads to acceleration of the photochemical reaction once the inhibition is over—leading to an overall increase of the signal-to-noise ratio and, hence, analytical sensitivity of the assay.

In embodiments, the additives may include an ascorbic acid or a certain derivative thereof, one or a combination of antioxidants, alcohols, surfactants, sugars, organic and inorganic reducers, and scavengers of reactive oxygen species (ROS) as specified above.

In other embodiments of the invention, the substrates of the photosensitized chemical reaction may include derivatives of OPD, Diaminobenzidine (DAB), olefin, luminol, dioxetane, and benzofurane.

In embodiments, examples of a photosensitizer include a phenazine, a phenazine derivative, a 2,3-diamino-phenazine, a benzidine, a benzidine derivative, an eosin, an eosin derivative, an erythrosine, an erythrosine derivative, a toluidine blue, a crystal violet, a merocyanine 540, Rose Bengal, a methylene blue, a porphyrine, a hematoporphyrin, a porphyrine derivative, a phthalocyanine, a phthalocyanine derivative, an aluminum phthalocyanine tetrasulfonate (AlPCS) derivative, a riboflavin, and a quantum dot.

In embodiments, the substrate or the photosensitizer may be embedded in microparticles, nanoparticles or liposomes. Some or all steps of the process may be carried out in a single mixture of all solutions without physical separation of bound and unbound fractions of reagents.

The method is further described as it applies to a commercially available ELISA tests, which is meant only to be illustrative of the method and not to limit the scope of the claims that follow. One skilled in the art would recognize the utility of the present invention in other assays utilizing photochemical reactions. The description of other than ELISA methods is also provided.

The methodology of the assay of the invention may closely follow the protocols of commercially available immunoassay and hybridization assays. It is well understood by those skilled in the art that the present invention will have numerous applications in the field of immunoassay, ligand-receptor, hybridization assays and high throughput drug screening and the scope of the invention will become more apparent through the following examples.

In one embodiment, described is a method for increasing ELISA sensitivity by utilizing a photochemical amplification step. It consists of two critical steps. During the first step, a conventional horseradish peroxidase (HRP)-mediated assay may be used. An enzymatic label such as HRP may be used to catalyze the conversion of oxidation of a common chromogenic HRP substrate such as orthophenylenediamine (OPD) into a product of a photochemical reaction, a photosensitizer 2,3-diaminophenazine (DAP) (reaction 2).

During the second critical step, the reagent solution containing the additives described above is added. The HRP substrate solution containing the product of enzymatic reaction, 2,3-diaminophenazine (DAP), may be irradiated by light within a predefined range of wavelengths. (reaction 3). In this example, the preferred range of wavelengths is from about 400 nm to 500 nm. The term "about" is used herein and throughout the specification to describe +/−30% deviation from the cited parameter. Irradiation of the samples with such light leads to DAP-catalyzed drastic increase in DAP concentration (autocatalytic photochemical reaction). This reaction is delayed until the additives are depleted, leading to acceleration thereof afterwards.

Thus a two stage process takes place:

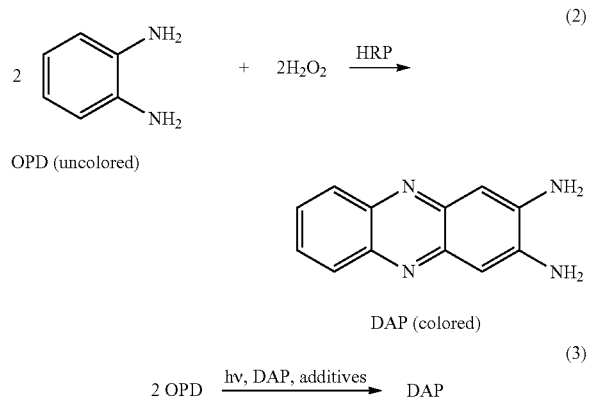

$$2 \text{ OPD} \xrightarrow{hv, \text{DAP, additives}} \text{DAP} \quad (3)$$

The assay of the present invention including ELISA and the photochemical amplification as described may be called ELISA+PMI.

While the previous assays (described in the '703 patent and the '842 application) were shown to increase the sensitivity up to 8-fold, the present invention is shown to achieve as much as a 100-fold sensitivity increase. Furthermore, the use of the PMI step as described here allows increasing of the signal-to-noise ratio and decreasing of the limit of detection (LOD) of clinically significant analytes such as *Clostridium difficile* toxin A, a *Clostridium difficile* toxin B, HIV-1 p 24 antigen, Prostate Specific Antigen (PSA) and Hepatitis B surface antigen (HBsAg) and other physiologically active substances 20- to 100-fold, as compared to conventional ELISA.

In ELISA-type assays, as an initial step, at least one interactive material, typically an antibody, may be retained or bound to a support phase, which may comprise a plate, a body of beads or other particulate matter, tubes, rings, a porous matrix (such as those used in Western Blot techniques), or other materials of various design known to those skilled in the art.

Next, a sample of the biological fluid to be tested may be added to the plate. Examples of the fluid samples may include blood, serum, plasma, different body fluids, food extract, environmental samples, cell culture, etc. If the biological fluid contains the target analyte (antigen) then an antibody-antigen complex is formed.

Next, an interactive material (such as an antibody to the specific antigen) may be added to the plate. This second antibody may be labeled with biotin, and then enzyme conjugate of streptavidin may be used, or with various enzymes that are well-known in the art. Of particular relevance to the present invention, the enzyme used becomes part of a complex that reacts with a substrate to produce a product which is detectable using colorimetry, fluorometry or chemiluminescence. As an example, the PerkinElmer HIV-1 p24 kit uses a streptavidin protein labeled with HRP which reacts with OPD to form DAP, which produces a yellow color that is detectable by absorbance (optical density) readers.

In the conventional methods, a stopping agent would now be applied after a suitable reaction time. As opposed to prior art, the assay of the present invention delays or in some case avoids entirely the use of the stop solution. After enzymatic reaction, a reagent solution containing additives of the present invention is added. Light irradiation is then applied. The photochemical reaction is temporality inhibited by the additive as described above. Once the additive is depleted, the photochemical reaction of OPD oxidation is accelerated to produce the product, DAP.

The invention also describes methods for increasing the sensitivity of the assay including the photochemical reaction. The invention further describes a method for increasing the rate of the photochemical reaction by the addition of one or more novel reagent solutions described herein. Further, the invention comprises a method for increasing both the sensitivity of the assay including the photochemical reaction and the rate of the photochemical reaction.

In embodiments, the peroxidase enzyme is horseradish peroxidase. Furthermore, the light irradiation may activate a peroxidase reaction product of OPD oxidation. The reaction product of oxidation may be 2,3-diaminophenazine (DAP).

In order to increase the slope of the calibration curve, and thereby lower the detection limit of determination of HRP, certain additives to the OPD substrate solution before or after the enzymatic reaction step may be added. These substances restrain the photochemical formation of DAP at low HRP concentrations and, hence, at small amounts of DAP, produced during enzymatic reaction. That is, the additives are inhibitors of the reaction of OPD photooxidation (reaction 3) and they have to be depleted after a certain period of time. The reaction (3) proceeds through the formation of either OPD intermediates, for example OPD-cation radical, or reactive oxygen species (ROS)-intermediates. Addition of inhibitors of the reaction (3) to the OPD substrate solution may result in the interaction of inhibitor and reactive intermediate compounds. This leads to the restraining of the signal increase at initial stages of the reaction when inhibitor is yet to be depleted. A schematic presentation of the reactions between inhibitor X and intermediates is as follows:

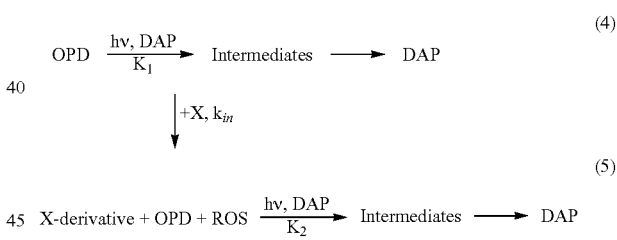

where X refers to the inhibitor interacting with intermediate compounds to give non- or less reactive X-derivative. Inhibitor X may inhibit the photochemical reaction until the moment when amount of X is enough to restrain the formation of DAP from intermediate compounds. Since the addition of X leads to decrease in the amount of intermediates produced during the DAP-photosensitized reaction, the initial rate of this reaction will depend on the concentrations of X and DAP. That is, the lower DAP concentration, the lower initial rate of the photochemical reaction. Therefore, the light screening or quenching effects at higher DAP will be compensated by even more pronounced effect of the decrease in the rate of this reaction at lower DAP concentrations caused by the addition of the compound X. By another words, X is an organic compound added to temporally inhibit photooxidation of OPD. Depletion of X is DAP concentration dependent, and this depletion is followed by the increased reaction rate of OPD autocatalytic oxidation (that is, $K_2 > K_1$).

In embodiments, the reagent solution comprises inhibitors X (additives) which may include one or a combination of antioxidants, alcohols, surfactants, sugars, organic and inorganic reducers, and scavengers of reactive oxygen species (ROS).

Antioxidants may be classified into several categories based on their occurrence, structure, mode of action, kinetics, and solubility. These categories may include vitamins, hormones, steroids, saponines, carotenoids, enzymes, glutathione, minerals, phenolics, and lipid associated chemicals. These are also classified as enzymatic and non-enzymatic antioxidants. Ascorbic acid (Vitamin C) and α-tocopherol (Vitamin E) are two vitamins that belong to non-enzymatic class of antioxidants.

When the reagent solution includes one or more antioxidants, such antioxidants may act as singlet oxygen quenchers, free radical scavengers, reducing agents or hydrogen donors. Suitable examples of antioxidants may include ascorbic and iso-ascorbic acids and their derivatives (such as ascorbates and iso-ascorbates, ascorbic acid palmitate, stearate, and the like), tocopherols and trienols (alpha-, beta-, gamma- and delta-tocopherols and trienols), their derivatives and synthetic soluble tocopherol analogs similar to Trolox, flavanoids (myricetin, quercetin, rutin, kaempferol, and the like), antioxidant phenolic compounds other than flavanoids (BHA, BHT, TBHQ tert-butyl phenol, gallic acid, caffeic acid, and similar), thiols and hydrosulfites (mercaptoethanol, L-cystein, dithiothreitol, dithionite, dithioerythritol and the like), carotenoids (xanthopylls and carotenes), melatonin, uric acid and derivatives, ubiquinones and quinones, lactates, steroids, NADH and NADH analogs, calcium antagonists, vitamin B6, aspirin, steroids pyrrolopyrimidines, ebselen, metallothioneins, metalloporphyrins, antioxidant mixtures, and enzymatic reactive oxygen species (ROS) scavengers such as superoxide dismutase (SOD), superoxide reductases, catalase, thioredoxin reductase, alkenal/one oxidoreductase, and peroxiredoxins.

Ascorbic Acid and its Derivatives

For the purposes of the present invention, the following compounds may be used as the additive in the reagent solution as described by formula (1)

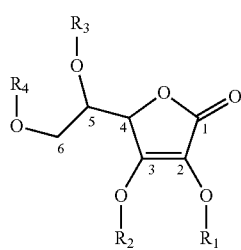

(1)

wherein the additive is an ascorbic acid or a derivative thereof obtained by at least one substitution at position 2, position 3, position 5, position 6 or any combinations thereof with at least one group of atoms selected from a group consisting of an anion group of atoms, an aliphatic group of atoms not exceeding 16 carbon atoms, and an aromatic group of atoms not exceeding 16 carbon atoms.

Ascorbic acid and its derivative the chemical structure of which are shown above exhibit powerful antioxidant activity in aqueous medium. Note that ascorbic acid is a compound of formula (1) in which R1, R2, R3, R4 are hydrogens. A number of ascorbic acid derivatives with substitutions at any one or a combination of positions 2, 3, 5 and 6 retaining their antioxidant activity have been reported in the literature. For the purposes of the invention, it is suggested to use those ascorbic acid derivatives, which (i) retain their antioxidant properties and (ii) present in aqueous solution in the forms described below.

In embodiments, ascorbic acid derivatives may be those wherein one or several modifications of ascorbic acid are present: R1, R2, R3, and R4 hydrogens may be substituted by groups of atoms selected from the group consisting of glucoside, glucopyranoside, phosphate, sulfate, lactate as well as various alkanoyl ethers and esters. Non-limiting examples of these include compounds with carbon atom chains including anywhere between 1 and 16 carbon atoms, such as for example ethyl, acetate, lactate, butyrate, caproate, octanoate, decanate, dodecanoate, oleate, myristate, palmitate, stearate and their mono- and poly-unsaturated counterparts.

These derivatives may encompass a variety of chemical entities ranging from simple salts (eg. Na, Mg, Ca, Fe, phosphate, sulfate) to derivatives such as O-substituted sugars (glucoside), as well as various alkanoyl ethers and esters mentioned above.

Modification of ascorbic acid by substituting at the positions 2, 3, 5, or 6 of the ascorbic acid ring contributes to its stabilization as an antioxidant. Ascorbic acid derivatives may retain the same activity exhibited by ascorbic acid. For example, the antioxidant activity is preserved for O-substituted ascorbic acid derivatives at position 2—such as in ascorbic acid 2-glucoside, ascorbic acid 2-phosphate, and ascorbic acid 2-sulfate. The antioxidant activity is also preserved or even increased for various 6-O-alkanoyl-ascorbic acids such as ascorbyl-6-octanoate, L-ascorbyl dodecanoate, ascorbyl palmitate, ascorbyl-2,6-dipalmitate, ascorbyl-5,6-dipalmitate and Ascorbyl-6-stearate. The above mentioned compounds can be an L- or R- or racemic mixtures.

Further derivatives of ascorbic acid that may be useful for the purposes of the present invention include Alkali, alkaline-earth, transition metals (for example sodium ascorbate, (+)-Magnesium L-ascorbate, Calcium L-Ascorbate etc).

In addition, those derivatives of ascorbic acid are useful for use with the assay of the invention which contain anion groups of atoms consisting of halogens and other non-metals (for example 2-Phospho-L-ascorbic acid trisodium salt, L-ascorbic acid 2-phosphate, Magnesium salt, L-ascorbic acid 2-sulfate, etc).

Aliphatic and/or aromatic groups or atoms as substitutes for positions 2, 3, 5, 6 or combinations thereof also fall under the definition of ascorbic acid derivatives useful for the purposes of the invention. In some embodiments, such groups of atoms may include anywhere between 1 and 16 carbon atoms therein.

Examples of useful ascorbic acid derivatives containing aliphatic groups of atoms with or without heteroatoms include 3-O-Ethyl ascorbic acid, Ascorbyl-2-glucoside, L-Ascorbic acid acetonide, Ascorbyl-6-octanoate, L-Ascorbyl Dodecanoate, Ascorbyl-6-palmitate, Ascorbyl-6-stearate, ascorbyl-2,6-dipalmitate and Ascorbyl-5,6-dipalmitate.

Examples of ascorbic acid derivatives containing aromatic group of atoms include 5-(phenylethynyl)uracil-2,3-di-O-benzylated 1-ascorbic acid derivative (as described by Gazivoda T et al. The novel C-5 aryl, alkenyl, and alkynyl substituted uracil derivatives of L-ascorbic acid: synthesis, cytostatic, and antiviral activity evaluations. Published in Bioorg Med. Chem. 2007 Jan. 15; 15(2):749-58 incorporated herein by reference in its entirety).

Further examples of ascorbic acid derivatives with aromatic groups of atoms include pyrimidine and purine derivatives of L-ascorbic acid (as described by Raić-Malić et al. Novel pyrimidine and purine derivatives of L-ascorbic acid: synthesis and biological evaluation. J Med. Chem. 1999 Jul. 15; 42(14):2673-8 incorporated herein by reference in its entirety.

Finally, yet another group of derivatives of ascorbic acid may be used for the present invention, namely an O-alkyl ascorbic acid derivatives containing at least one substitution of R3 at position 5, R4 at position 6, or both R3 at position 5 and R4 at position 6 by a group of $(CH_2)x$-$CH_3$, where x is a number of ($CH_2$) elements, which may be 1 or more but not exceeding 14.

It is also important to select the derivative of the ascorbic acid which maintains suitable solubility in an aqueous solution. Solubility is defined herein as an ability of one compound to be present in the solution and not precipitate. In order for the additive of the present invention to be effective, it may be present in the aqueous solution in at least one of the following forms: 1) the additive may be simply present in water, 2) the additive may be present in aqueous solutions and dissolved in the form of amphiphilic structures such as micelles, liposomes and vesicles formed by another compound or 3) the additives may be present in aqueous solution in the form of self-assembled amphiphilic structures (supramolecular aggregates) such as micelles, liposomes and vesicles. Such supramolecular aggregates of ascorbic acid derivatives allow retention of the antioxidant activity of ascorbic acid. The examples of micelles formed by another than the additive of the present invention are micelles formed by detergents such as Tween-20, Tween-80, Triton X-100, Cetyl trimethylammonium bromide (CTAB), and Sodium dodecyl sulfate (SDS). While ascorbic acid and its salts are water-soluble, some ascorbic acid hydrophobic derivatives carrying hydrocarbon chains (e.g., ethers and esters at positions 2, 3, 5, or 6 of the ascorbic acid ring) may form self-assembled supramolecular aggregates such as micelles and vesicles and may be present in aqueous solutions in concentrations up to 50% (which is equal to about 1 to about 10 moles per liter). Since the effect of the present invention is generally observed at concentrations of additives in aqueous solutions starting from about $10 \times 10^{-6}$ M and above, they may be present in an aqueous solution in one of the above described forms.

The term about is used herein and in other parts of the specification to describe +/−25% variation of the cited value.

Other Compounds of the Reaction

Examples of suitable alcohols may include ethanol, methanol, glycerol and ethyleneglycol (HO—$CH_2$—$CH_2$—OH) and their polymer analogs such as polyethyleneglycol.

Examples of suitable sugars may include monosacharides (erythrose, arabinose, ribose, glucose, mannose, xylose, fructose, galactose, and the like), disaccharides (sucrose, maltose, cellobiose, lactose, and the like), oligosaccharides (raffinose, stachyose, cyclodextrins, and the like), and their polymer analogs polysaccharides (amylose, amylopectins, glycogen, cellulose, their derivatives, and the like).

Examples of suitable reactive oxygen species (ROS) may include $^1O_2$, $.O_2^-$, $H_2O_2$, ROO., $OCl^-$, $ONOO^-$, NO, and their unstable intermediates. The following reagents, which are known to be very effective scavengers of hydroxyl radicals, may be selected for scavenging of hydroxyl radicals: ethanol, n-butanol, iso-propanol, 2-propanol and ethyleneglycol, DMSO, methional, sodium benzoate, sodium formate, mannitol.

Examples of suitable scavengers of superoxide anion $O_2^{.-}$ may include superoxide dismutase (SOD), an enzyme that catalyzes dismutation of superoxide to hydrogen peroxide.

Prior to irradiating a sample with light, one or a combination of the aforementioned reagents may be added.

The step of irradiating the enzymatic reaction components and additives added to these components with light may include providing such light within a predefined range of wavelengths. In case of above described DAP, the redefined range of wavelengths includes a visible light spectrum. The time of exposure of the sample to irradiation with light may vary depending on light intensity.

One or more fluid samples may be irradiated simultaneously by a suitable single or plural source of light, such as an array of light emitting diodes, a xenon lamp, a laser, a low power blue luminescent lamp, an array of such lamps placed at a predefined distance between each other. In some embodiments, an air- or liquid-based cooling system such as a cooling fan may be utilized. Activation of such cooling systems may be done manually or automatically—for example based on the reading of a temperature sensor. Other accessories may also be utilized as known to those skilled in the art.

One suitable detection technique is colorimetric detection using a photometer or optical density reader. Using the PerkinElmer HIV-1 p24 kit as an example, the absorbance or optical density (OD) of the sample may be measured at 450 nm, which indicates the concentration of DAP, and therefore the presence of HIV p24 antigen in the blood sample. Of course, one skilled in the art would recognize that the OD may be measured at a wavelength that detects the presence of DAP formed in any particular assay method.

One or more acids may be added to the mixture after light irradiation as stop solutions. Such acids include, but are not limited to sulfuric acid or hydrochloric acid. The measuring wavelength of the DAP after addition of the stop solutions should be 492 nm.

Concentration of the final product of the photochemical amplification reaction, such as DAP in the described example, may also be determined by measuring fluorescence without or with addition of the fluorescence converter solution containing nonionic or ionic surfactants. Suitable examples of surfactants may include polyoxyethylenesorbitanmonolaurate (Tween-20), octylphenoxypolyethoxyethanol (Triton X-100, and polyethoxyethylene sorbitanmonooleat (Tween-80).

The enzymatic reaction of the assay of the present invention may proceed under multiple conditions such as over various periods of time, at altered temperature, pH, OPD concentration, or with the addition of other additives disclosed herein. In an exemplary embodiment, the enzymatic reaction may proceed at room temperature in 0.1 M phosphate-citric acid buffer, at a pH of about 5.0 with a total enzymatic reaction time of about 30 minutes.

The increased production of DAP in the described example may be achieved without a corresponding increase in background noise. Therefore, the utility of the method is greatly increased over the prior art.

In accordance with another aspect of the invention, there is provided a reagent kit or package of materials for accomplishing an assay of the invention. The kit may include a solid support having an anti-analyte antibody attached to this support. The antibody may be selected to have affinity to the analyte. The kit may also include reference standards for the analyte, for example, one or more analyte samples of known concentration. The kit may further include other reagents or solutions, such as buffers, or labeled specific antigens, antibodies or complexes thereof useful in carrying out the assay. The kit may also contain a reagent solution. The components of the kit may be supplied in separate containers, for example, vials, or two or more of the components may be combined in a single container.

In another aspect of the invention, described is an assay for determining the presence of an analyte. The analyte may be a HRP conjugate, a Hepatitis B Surface Antigen, an HIV p24 Antigen, a p50 recombinant protein, a NKjBp50 homodimer, an RNA, a DNA, a mRNA, a cDNA, a Prostatic Specific Antigen, a Clostridium difficile toxin A, a Clostridium difficile toxin B, a Rotavirus, an Anthrax (Bacillus anthracis), an Arenaviruse, a Clostridium botulinum toxin, a Brucella specie, a Burkholderia pseudomallei, a Chlamydia psittaci, a Vibrio cholerae, an Ebola virus, an Escherichia coli O157: H7, a variola major, a Staphylococcal enterotoxin B, a Francisella tularensis, a Salmonella, a Rickettsia prowazekii, a Yersinia pestis, a Cryptosporidium parvum, and a Shigella. One skilled in the art would recognize that there are many other substances including biological warfare, environmental- and food chain-threat agents that can be determined using the method of this invention and thus the list above is not meant to limit the scope of this invention.

In another aspect of the invention, the PMI step may be used not only for ELISA-type assays but also for other photosensitizer- or enzyme-mediated assays such as ligand-receptor assays, hybridization assays, immunohistochemistry, in situ hybridization and membrane-based assays: blotting analysis and immunochromatography tests. In these enzyme-mediated assays, after conducting the conventional assay, the HRP conjugate may be detected using OPD substrate solution followed by the photochemical amplification step of the invention as described above.

In another aspect of the invention, after conducting a conventional assay, the HRP conjugate may be detected using OPD substrate solution followed by the photochemical amplification step of the invention including the use of other than OPD substrate and the reagent solution as described above. In another aspect of the invention, OPD derivatives may be used as a substrate of enzymatic catalytic reaction.

In another aspect of the invention, after conducting a conventional assay, the HRP conjugate may be detected using other than OPD substrate solution during the enzymatic reaction (the product of which is a photosensitizer), followed by the photochemical amplification step including the use of either OPD substrate solution or other than OPD substrate and the reagent solution as described above.

In embodiments, the substrate of HRP-mediated reaction may be a dye-tyramine complex, and the product of this reaction may be a photosensitizer. Suitable photosensitizers may include a fluorescein-tyramine, an eosin-tyramine and an erythrosine-tyramine.

Still additional steps of the invention may alternately include conducting the enzymatic reaction on the surface of membranes, such as for example nitrocellulose, nylon, and paper. In some aspects of the invention, color changes or color spots caused by the addition of dyes or chemicals which result in the production of colors, may be viewed or detected by photographing or by eye.

After conducting the enzymatic reaction on the surface of the membrane, such membrane may be washed with a rinsing buffer, and then the substrate solution containing the additives of the present invention may be added. The reagent solution may comprise a mixture of ascorbic acid and a nonionic surfactant, or an alcohol and a nonionic surfactant, or any other combinations of the additives of the present invention as described above. In still another step, the product of the enzymatic reaction may be taken out of the solution, placed in the substrate solution and irradiated by light.

The instant invention may have multiple uses. For example, one or more of peroxidase molecules may be used as a label in enzyme immunoassay as well as in blotting analysis or in immunohistochemistry. The peroxidase activity may also be detected by the method described in this invention in assays including but not limited to phagocytosis, cell burst, oxidative capacity of cells and other methods known to those in the art.

Example 1

Determination of Diaminophenazine in Buffer Solution

In this system, various amounts of the photosensitizer Diaminophenazine (DAP) were added to the OPD substrate solution, and the solution was illuminated. One can see that this system mimics a photosensitizer (dye)-mediated analytical assay, in which the amount of the analyte is determined. In this case, DAP, DAP derivatives or other photosensitizers may be used as a label for the entities having an affinity to the analyte to be detected.

The procedure for conducting photoamplification experiments with compounds added to the OPD substrate solution was as follows. Briefly, 30 µl of the reagent solution (additives) was added to the 100 µl of OPD substrate solution (0.1 M phosphate-citrate buffer, pH 5.0), containing various amounts of DAP as a primer. After 30 min incubation, the samples were irradiated by visible light with wavelengths between 400 nm and 500 nm for various times using a "high" power Device 1 for even illumination of large surfaces, high power defined as between 1.0 and 2.0 lumen/centimeter$^2$/steradian light intensity. Then, the optical density of the samples was measured using a standard spectrophotometer or standard optical density reader.

FIG. 1A shows calibration (standard) curves for the detection of DAP primer added to the OPD substrate solution in double dilution at various times of the illumination in the absence of additives. As can be seen in FIG. 1A, the background (no DAP added) increases with the illumination time significantly. This feature of the DAP calibration curves affects the performance of the assay because in this case limit of detection (LOD) of the assay, defined as double the value of the background signal, increases with the illumination time.

Figure 1B:
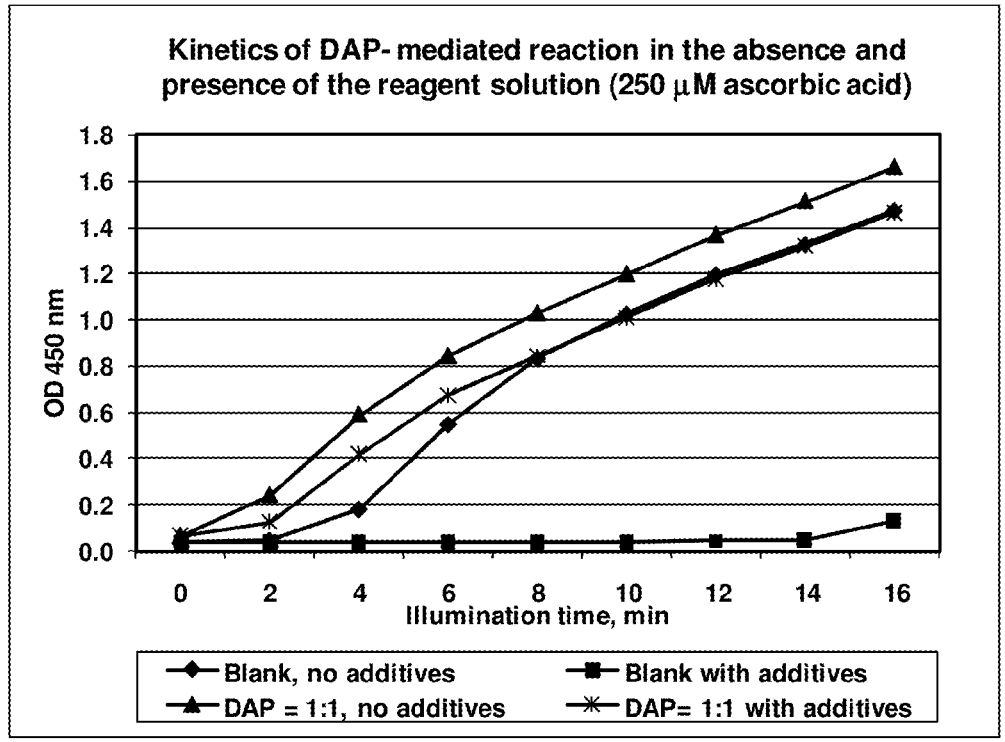

In order to circumvent this undesirable effect, some additives which are the inhibitors or retarders of the photochemical photosensitized reactions may be used (see above). FIG. 1B illustrates the effect of ascorbic acid (AA) on the kinetics of the DAP-mediated photosensitized reaction. In the presence of AA the increase of the background with illumination time is significantly lower than that when no additives are added to the OPD substrate solution. A similar effect was observed using derivatives of AA, glycerol, ethyleneglycol and polyethyleneglycols (see Example 3).

Figure 1C:
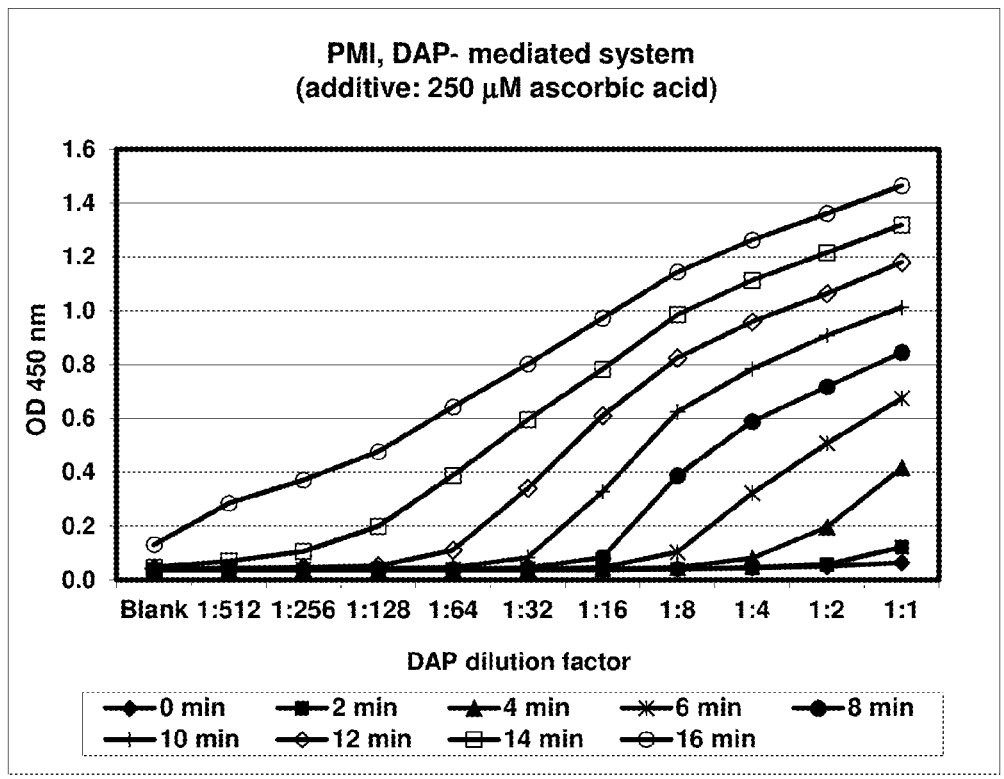
Figure 1D:
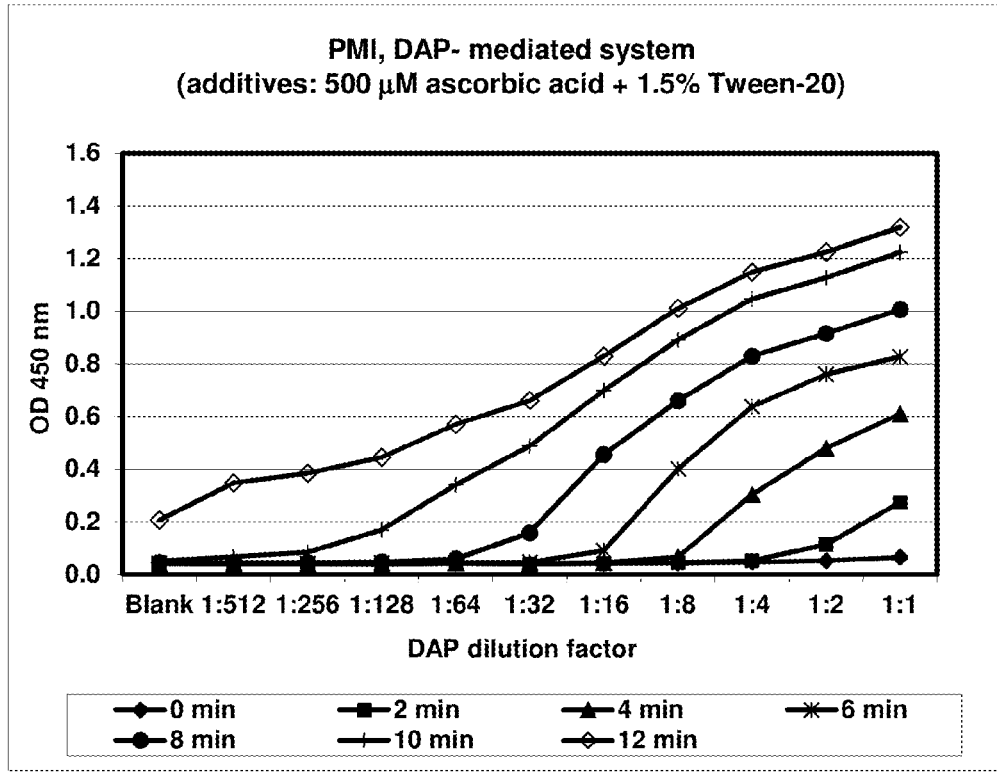

FIG. 1C shows the calibration curves for determination of DAP when a reagent solution containing 250 µM of AA is added. As can be seen in this Figure, the background increase is limited, and the detection limit (analytical sensitivity) of the assay is significantly lower than that for the assay with no additives added (see FIG. 1A). The same effect can also be achieved using a reagent solution containing 500 µM AA and 1.5% Tween-20 (FIG. 1D). The addition of the surfactant Tween-20 may lead to increase of the signal and decreasing of the illumination time. As can be seen in FIGS. 1C and 1D, the addition of the reagent solutions containing temporary inhibitor (retarder) of the photochemical reaction (ascorbic acid)

leads to drastic decrease of the limit of detection of the determination of the photo sensitizer, DAP.

Figure 4:
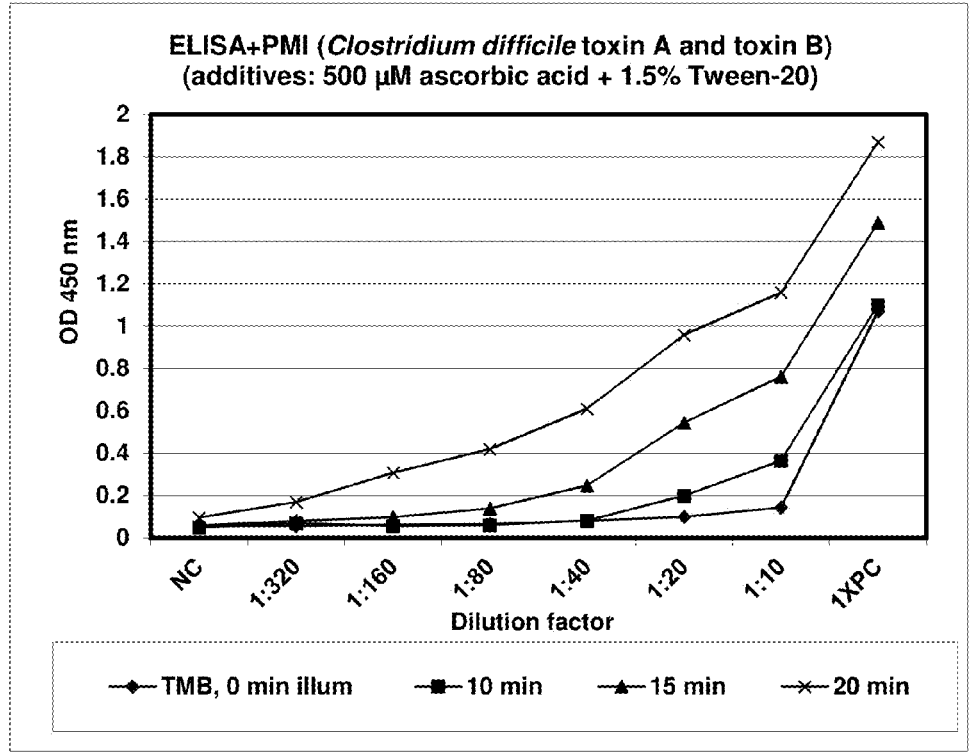
FIG. 4 shows calibration curves for determination of HIV-1 p24 antigen using conventional ELISA (0 min illumination) and ELISA+PMI at various times of illumination.

Indeed, the detection limit defined as double the value of the background of DAP determination depends on the background value and on the slope of the calibration curve. That is, the lower the background and higher the slope, the lower the detection limit of the analyte determination. The detection limit of the conventional assay without photochemical amplification can be estimated as 1:1 DAP dilution (FIG. 1A, 0 min illumination curve), whereas the detection limit of the assay with photochemical amplification when no reagent solution added (PAM, (method without the use of the reagent solution with additives of the present invention, FIG. 1A) is approximately 1:8 DAP dilution (FIG. 1A, 4 min illumination curve). The addition of the reagent solutions containing AA (or some other inhibitors and retarders of the photochemical reaction) to the OPD substrate solution changes the character of calibration curves for DAP determination drastically (FIGS. 1C and 1D), and as a consequence leads to decrease of the detection limit of the assay. Indeed, a more than 32- and 16-fold decrease of the limit of detection of DAP using a photochemical amplification with the reagent solution containing the additives of the present invention (PMI) (FIGS. 1C, 16 min illumination curve and 1D, 12 min illumination curve, respectively) occurs as compared to the PAM (method without the use of the reagent solution with additives of the present invention, FIG. 1A) and 256- and 128-fold increase as compared to the conventional assay (FIG. 1A).

Example 2

Determination of HRP Concentration in Buffer Solution

In this system, HRP conjugate concentration in the buffer solution is determined using the prepared calibration curves. In order to prepare the calibration curves for determination of HRP, OPD substrate solution was added to the HRP conjugate solutions at various concentrations, and after incubation, the solutions were illuminated for a certain period of time. One can see that this system mimics the last step of enzyme-mediated analytical assays, in which the amount of HRP bound to the well of the microtiter plate (as in ELISA-type assays) or membrane (as in blotting analysis) or cell surface (as in immunohistochemistry or in situ hybridization) is determined.

In more detail, to each test well of a standard 96-well microtiter plate containing 20 of the HRP conjugated antibody (PerkinElmer) at various dilutions in 0.01 M phosphate buffer, pH 7.0, 80 µl of OPD substrate solution was added. The HRP-mediated oxidation of OPD was carried out at room temperature in 0.1 M phosphate-citric acid buffer at pH 5.0. The reaction time was 30 min in all experiments. 30 µl of reagent solutions (additives) were added to the OPD substrate solution after the incubation step before illumination. After incubation period the substrate solution was irradiated using the illumination instrument for irradiation of large surfaces (Device 1, high power). The optical density of the samples at 450 nm was measured using an optical density microtiter plate reader.

Figure 2A:
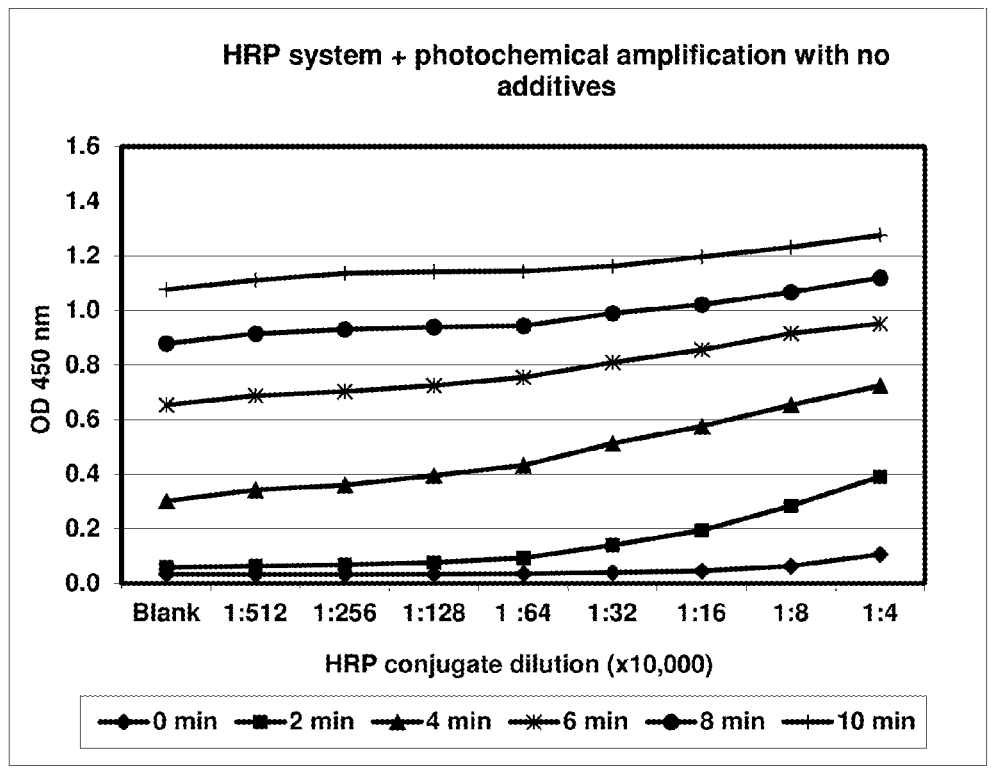
FIGS. 2A through 2D show calibration curves for determination of HRP conjugate in the buffer solution at various times of illumination in the absence (FIG. 2A) and presence of the reagent solutions containing 250 μM ascorbic acid (FIG. 2B), 250 μM ascorbic acid and 1.5% Tween 20 (FIG. 2C) and 500 μM ascorbic acid and 1.5% Tween 20 (FIG. 2D).

In FIG. 2A, the optical density of the background (no HRP in the sample) for the conventional procedure is in the range of 0.03-0.05. The measurement of the optical density by regular commercially available readers has an error on the order of ±0.01. In such cases, companies manufacturing diagnostic analytical kits define the detection limit of the assay relying on practical assumptions. In particular, the reasonable threshold value of the signal of the assay should be defined. In our case, the reasonable threshold signal can be equal to Background+0.03 for the conventional enzymatic determination. Therefore, as can be seen in FIG. 2A, 0 min illumination curve, the detection limit of the conventional assay is 1:40,000 dilution of the HRP conjugate. FIG. 2A also shows that the detection limit for HRP determination by the assay with photochemical amplification with no reagent solution containing additives of the present invention (PAM) at 2 and 4 minutes illumination is approximately 1:320,000 HRP conjugate dilution which is 8-fold lower than that of the conventional assay procedure (without illumination). One of the features of the FIG. 2A is that the slope of the HRP calibration (standard) curves decreases with increasing of the illumination time. This affects the performance of the assay significantly. As we mentioned above, the detection limit defined as twice the value of the background of HRP determination depends on the background value and on the slope of the calibration curve. That is, the lower the background and higher the slope, the lower the value of detection limit of the analyte determination.

Figure 2B:
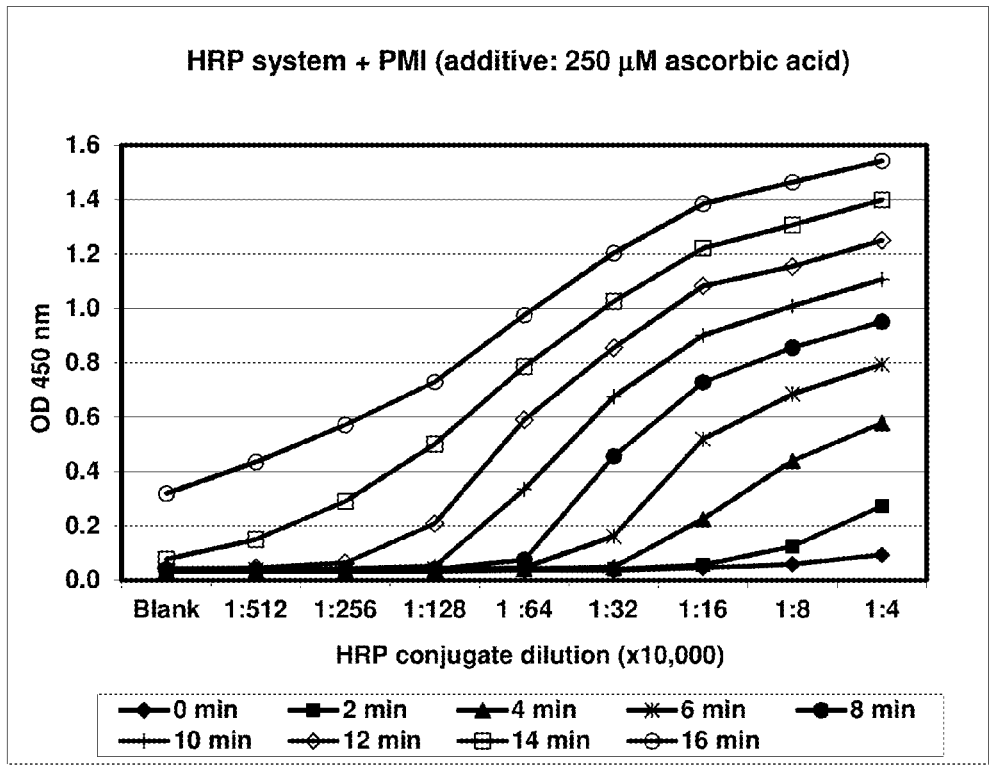
Figure 2C:
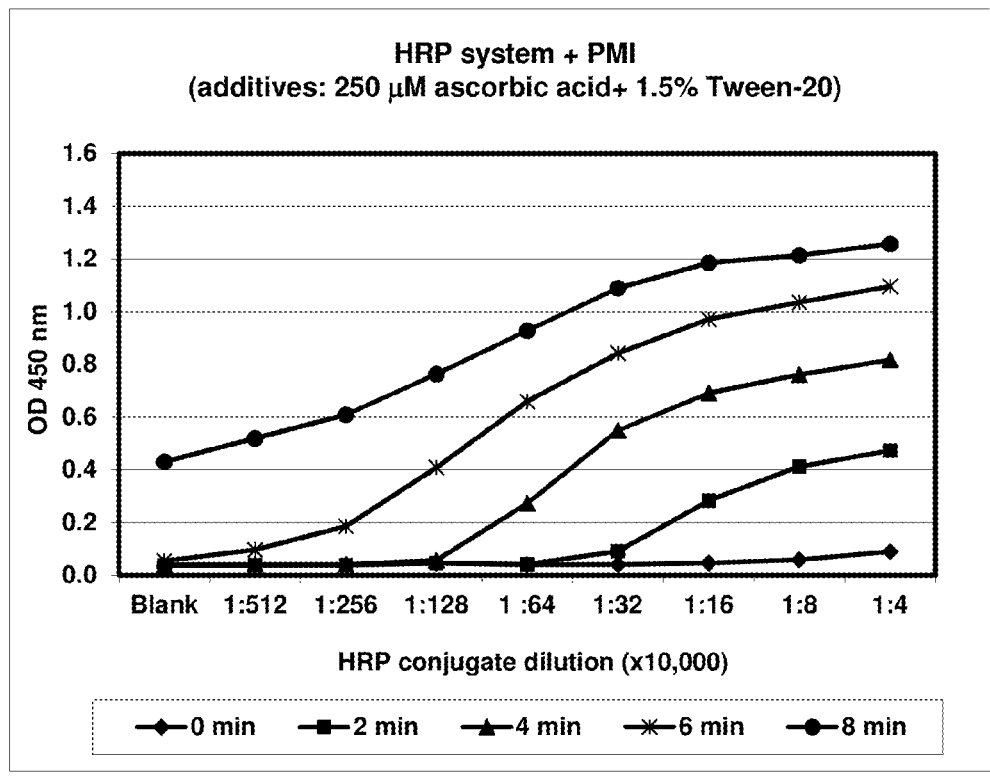
Figure 2D:
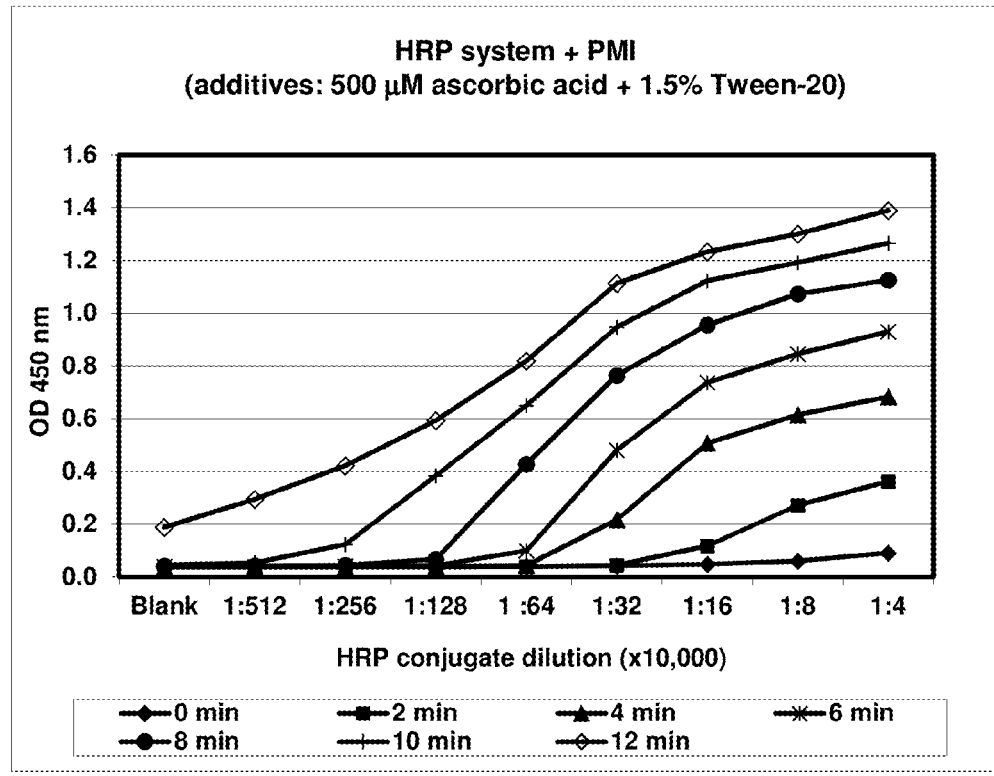

The addition of the reagent solution containing 250 µM ascorbic acid in phosphate-citrate buffer (PCB), pH 5.0 (reagent solution #1) to the OPD substrate solution after conducting the enzymatic step changes the character of the calibration curves for HRP determination (FIGS. 2B-D), and results in a drastic decrease of the detection limit of the assay. As can be seen in FIG. 2B, 14 and 16 min illumination curves, the detection limit of the assay can be estimated to be 1:5,120,000-1:2,560,000 of the HRP dilution, which is 128-64-fold less than the limit of detection of HRP conjugate as compared to the conventional procedure, and approximately 16-8-fold less than the detection limit of the PAM. FIG. 2C shows the effect of adding the reagent solution containing 250 µM ascorbic acid and 1.5% Tween-20 in PCB (reagent solution #2), which results in decrease in the limit of detection of the assay and increase in the rate of the photochemical reaction. One can further limit the increase of the background signal by using the reagent solution #3 containing as twice the ascorbic acid concentration as compared to the reagent solution #2 (FIG. 2D).

Example 3

Determination of HRP Concentration Using Reagent Solutions Containing Ascorbic Acid Derivatives and Materials Possessing Antioxidant Activity Calibration curves for determination of HRP were prepared in the same manner as described in the Example 2, except that reagent solutions that were added after performing the incubation step before illumination contained other than ascorbic acid compounds. The obtained results are presented in FIGS. 3A-C.

Figure 3A:
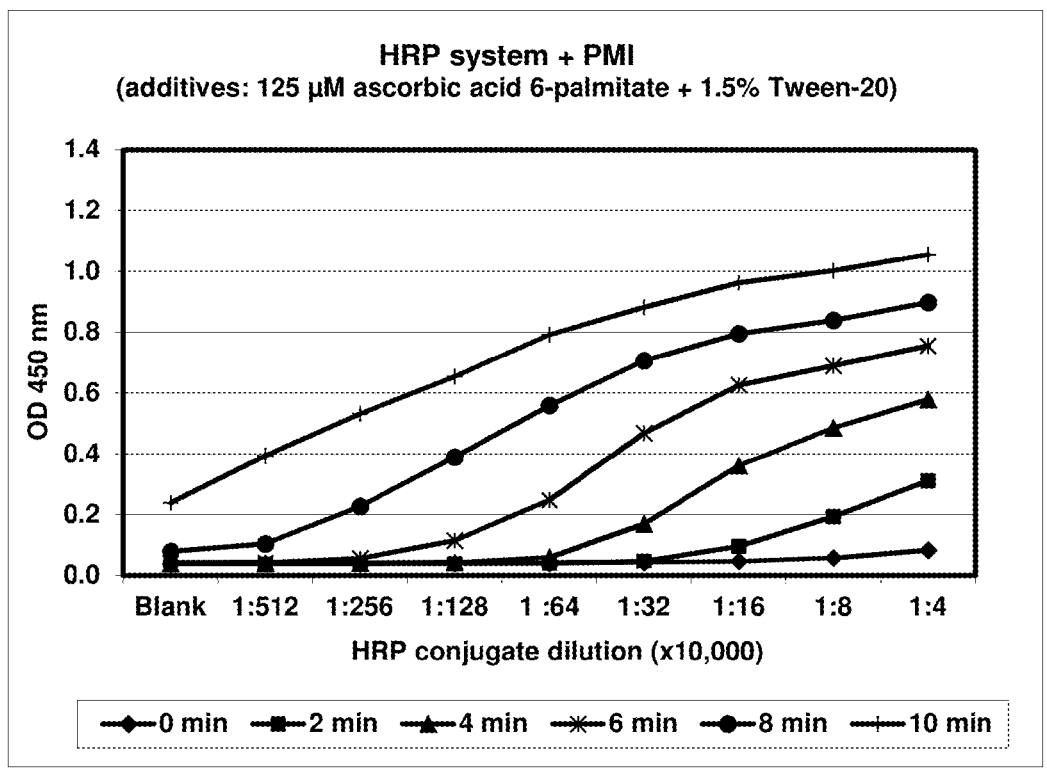
FIGS. 3A through 3C show calibration curves for determination of HRP conjugate in the buffer solution in the presence of the reagent solutions containing 125 mM ascorbic acid 6-palmitate and 1.5% Tween-20 (FIG. 3A), 250 mM isoascorbic acid+1.5% Tween-20 (FIG. 3B), and 18.6% glycerol and 1.5% Tween-20 (FIG. 3C).
Figure 3B:
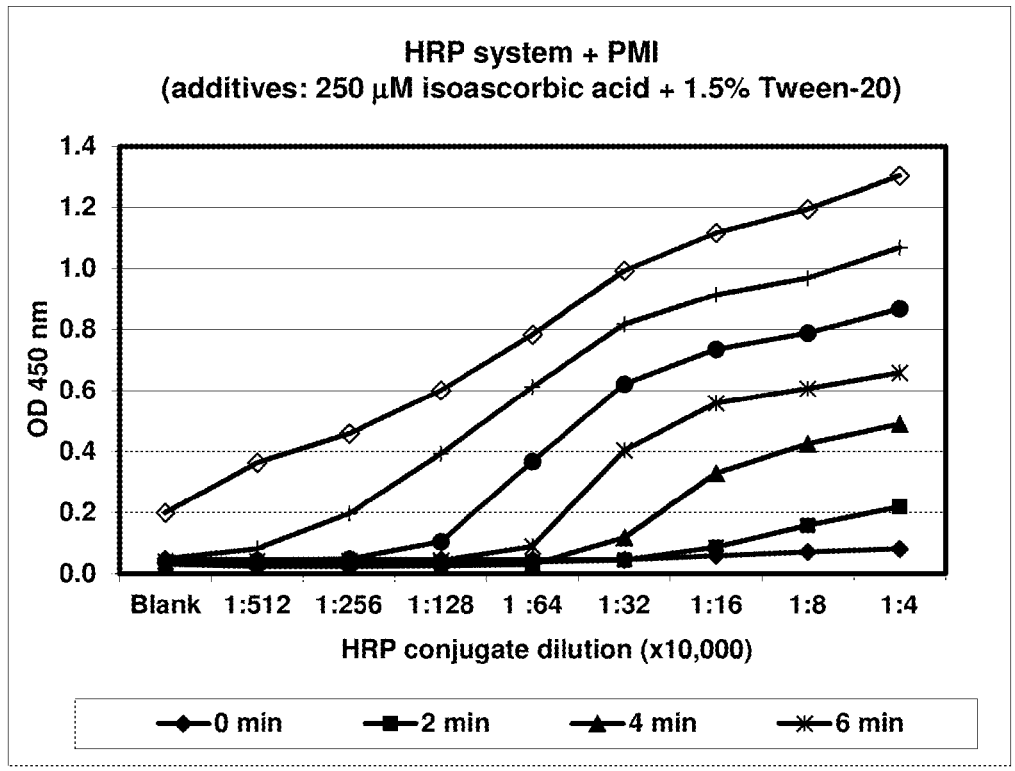
Figure 3C:
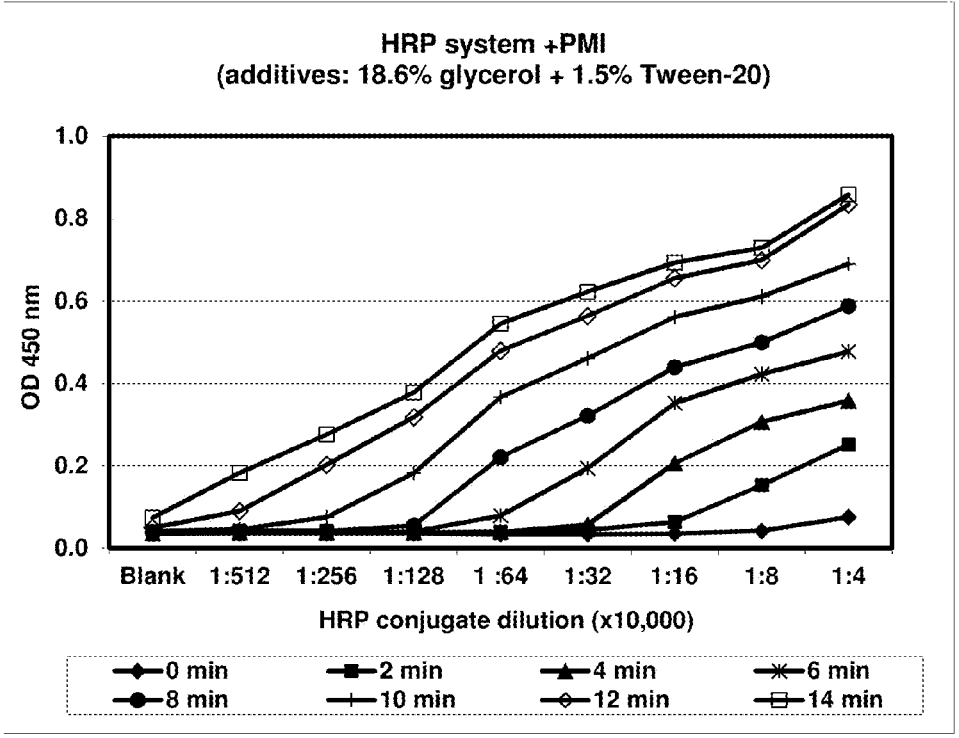

As can be seen in FIG. 3A, 10 min illumination curve, the addition of the reagent solution containing 125 µM ascorbic acid 6-palmitate and 1.5% Tween-20 in PCB to the OPD substrate solution results in decrease of the limit of detection (LOD) of the assay, which is between 1:5,120,000 and 1:2,560,000 of the HRP conjugate dilution, as compared to the conventional assay 64-128 fold. Comparable increase in the analytical sensitivity (decrease in LOD) was observed when the reagent solutions containing 250 µM isoascorbic acid+1.5% Tween-20 in PCB (FIG. 3B, 12 min illumination curve) and 18.6% glycerol+1.5% Tween-20 in PCB (reagent solution #4, FIG. 3C, 14 min illumination curve) were used.

Similar results were obtained using ethyleneglycol and polyethyleneglycols. We assume that some materials such as glycerol, ethyleneglycol and polyethyleneglycols may have reducing and antioxidant activity or may contain antioxidants as impurities. It should be emphasized that the addition of the aforementioned reagent solutions before performing enzymatic reaction leads to the decrease of the assay LOD as well.

Figure 5A:
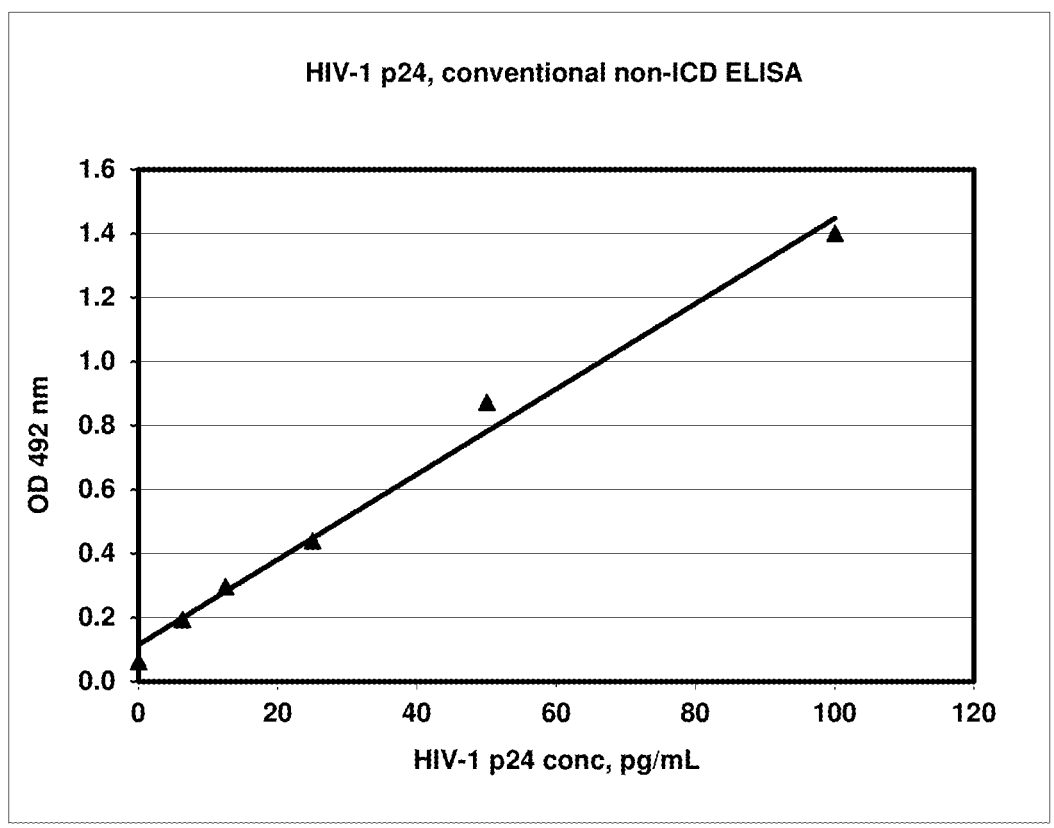
FIGS. 5A through 5D illustrate calibration curves for determination of HIV-1 p24 antigen using conventional non-ICD ELISA (PerkinElmer) (FIG. 5A), non-ICD ELISA+PMI (FIG. 5B), heat-mediated ICD ELISA (FIG. 5C), and heat-mediated ICD ELISA+PMI (FIG. 5D).
Figure 5B:
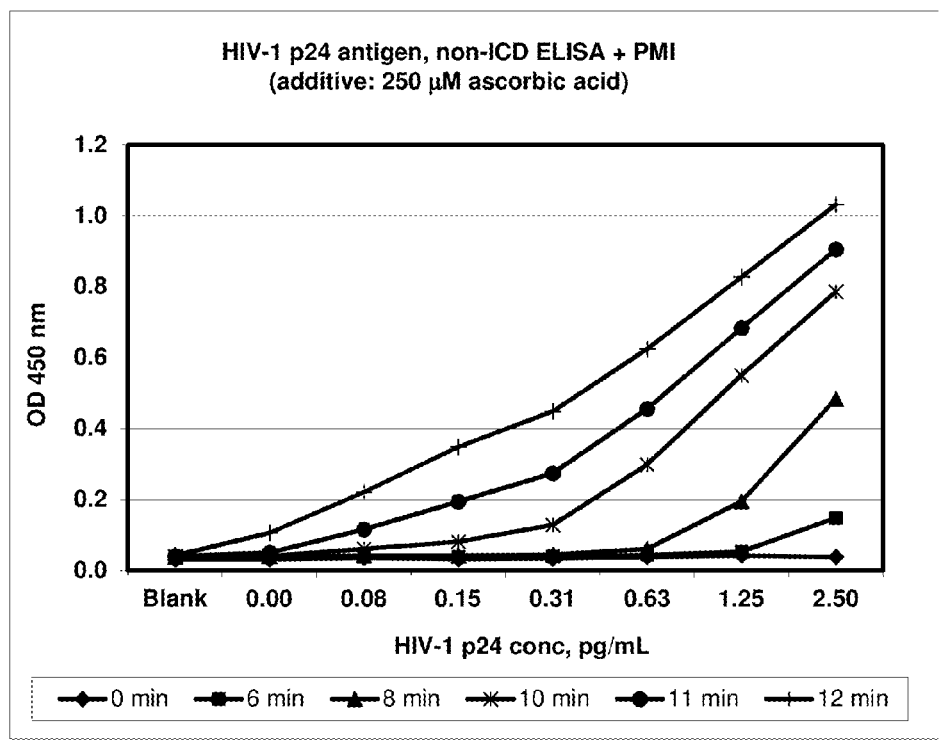
Figure 5C:
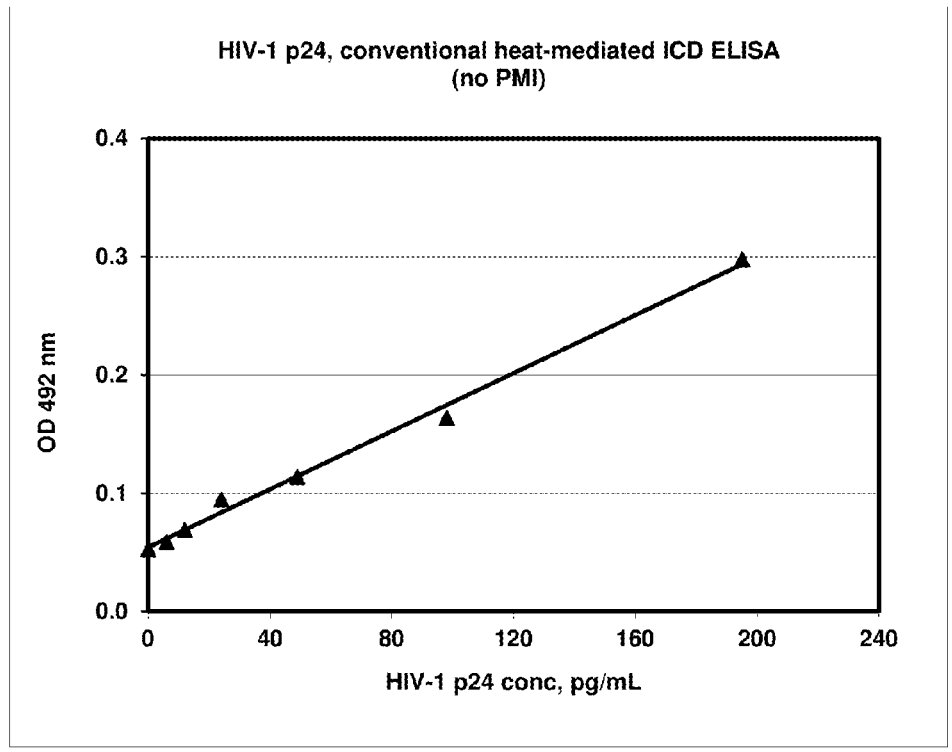

Example 4

Preparation of the Calibration Curve for Determination of *Clostridium difficile* Toxin A and Toxin B by PMI

*Clostridium difficile* bacteria is related to the same class of pathogenic bacteria as *Clostridium botulinum*, biological warfare agent. Cytoclone A+B ELISA kit reagents for determination of *Clostridium difficile* toxin A and toxin B were obtained from the Cambridge Biotech. Conventional ELISA procedure for the determination of the above antigens was performed according to the manufacturer's procedure. Briefly, the calibration curves for the *Clostridium difficile* toxin A and toxin B were prepared as follows: to each test well 100 μl of appropriate HRP conjugated antibody and 100 μl of negative and positive controls in various dilution were added. The mixtures were incubated for 60 minutes at 37° C. for toxin A+B detection. Wells were rinsed 5 times with washing buffer, and 100 μl of TMB substrate solution was added to each well. After 20 minutes incubation, the reaction was terminated with 50 μl of stopping solution. The absorbance at 450 nm was read using the Titerscan Multiscan reader.

Preparation of the calibration curves for the determination of the above antigens with PMI step involved carrying out the slightly modified conventional ELISA procedure and irradiation of the samples as described above. The modification of ELISA procedure was just in that OPD substrate solution was used instead of TMB substrate solution. After enzymatic reaction was finished, the reagent solution containing 500 μM AA and 1.5% Tween-20 in phosphate-citrate buffer was added to the OPD substrate solution. Then, samples being in 96-well microtiter plate were irradiated for various time and optical density or fluorescence of the samples was measured as described above.

The standard curves prepared by conventional ELISA and ELISA with PMI for *Clostridium difficile* toxin A and toxin B determination in the range of positive control dilutions from 1:320 to 1:10 are shown in the FIG. 4. According to the protocol of Cambridge Biotech Co. the cut-off line for detection of these antigens by the conventional ELISA procedure is 0.2 optical density values. Therefore, the detection limit for this method equals approximately to 1:5 positive control dilution. As can be seen in FIG. 4, the detection limit for toxin A+B determination using PMI equals to 1:300 dilution of the positive control. Thus, the sensitivity of the assay increases more than 50-fold when PMI is used.

Example 5

Preparation of the Calibration Curve for Determination of HIV p24 Antigen by PMI An ELISA kit for detection and quantification of HIV p24 antigen was obtained from Perkin Elmer Life Sciences (Boston, Mass.). This kit contains a 96-well microtiter plate the wells of which are coated with a highly specific mouse monoclonal antibody to HIV-1 p24. The immobilized monoclonal antibody captures both free HIV-1 p24 and that which has been released upon disruption of immune complexes in the serum/plasma sample. The captured antigen is complexed with biotinylated polyclonal antibody to HIV-1 p24, followed by a streptavidin-HRP (horseradish peroxidase) conjugate. The resulting complex is detected by incubation with ortho-phenylenediamine-HCl (OPD), which produces a yellow color that is directly proportional to the amount of HIV-1 p24 captured. The absorbance of each microplate well is determined using a microplate reader and calibrated against the absorbance of an HIV-1 p24 antigen standard or standard curve. Samples with absorbance values equal to or greater than the cutoff factor are considered initially reactive.

Conventional Non-ICD ELISA.

The HIV p24 ELISA test was performed in accordance with the manufacturer's instructions. Analytical sensitivity of the conventional ELISA test was determined via the least squares fit to the standard curve at an absorbance equal to the cutoff defined by the manufacturer (i.e., mean negative control OD+0.050). The conventional ELISA calibration curves for quantification of HIV-1 p24 antigen were provided by the manufacturer and prepared by us. The detection limit was calculated by us as recommended by the manufacturer and by using regression analysis, and showed that they are equal to 3.5 and 4.5 pg/mL, respectively. These values are in agreement with that provided by the manufacturer for the detection limit of the conventional non-ICD ELISA test for HIV-1 p24 antigen, which is 3.5 pg/mL. The detection limits were also estimated as the analyte concentration corresponding to the twice the value of the background signal, and practically the same results were obtained. The calibration curve prepared for the conventional non-ICD ELISA test is presented in FIG. 5A.

Non-ICD p24 ELISA+PMI. In order to reach the maximum sensitivity of the ELISA+PMI, the conditions for performing the conventional assay were first optimized. This is because the conventional test conducted without any changes is rather "noisy", that is, it is characterized by a high level of non-specific binding of reagents. In the non-ICD ELISA+PMI assay, a high background signal may affect the performance of the test because the amplification of both signal and background may occur. Therefore, in order to reach the maximum signal-to-noise ratio in ELISA+PMI, the background (noise) signal should be as low as possible. With respect to this, the procedure for carrying out the conventional ELISA-based test was slightly modified. The assay steps were the same as for the conventional assay procedure described above, except decreased incubation time (10 min instead of 30 min in conventional assay) with OPD substrate solution was used. After a 10 min incubation step, 30 μl of the reagent solution #1 (250 μM ascorbic acid in PCB), was added to 100 μl of OPD substrate solution, and samples were irradiated using a powerful illumination Device 1. Calibration curves for determination of p24 antigen were prepared by double dilution of positive control in negative control (normal human serum). The calibration curves prepared using non-ICD ELISA+PMI under the above conditions and at various times of illumination are presented in FIG. 5B. The detection limit calculated as the analyte concentration corresponding to twice the value of the background signal using a regression analysis for the p24 antigen ELISA+PMI at 12 min of illumination, is equal to 0.08 pg/mL. Thus, the analytical sensitivity of the ELISA+PMI is approximately 44-fold higher than that for the conventional assay.

Heat-mediated ICD ELISA (Ultrasensitive ELISA without tyramide signal amplification) was suggested by us to increase the sensitivity of ICD ELISA+PMI as we did not receive significant signal amplification when using PMI with conventional Perkin Elmer ICD ELISA. The complex disruption and ELISA protocols from Ultrasensitive HIV-1 p24 assay (PerkinElmer) were adopted, but the tyramide signal amplification step was excluded. The calibration curve prepared for heat-mediated ICD ELISA test is presented in FIG. 5C. The detection limit for the heat-mediated ICD ELISA was calculated by regression analysis, and is equal to 40 pg/mL.

Figure 5D:
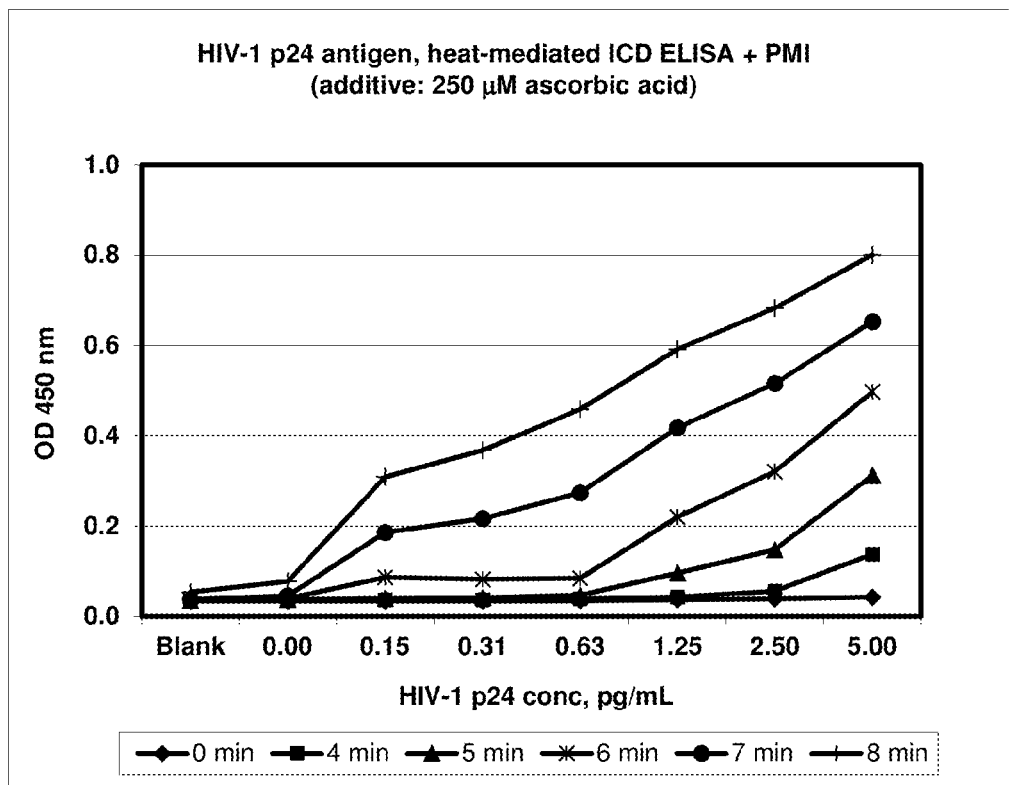

Heat-mediated ICD p24 ELISA+PMI. Heat-mediated ICD p24 ELISA steps were the same as for Ultrasensitive HIV-1 p24 assay (PerkinElmer), except that four changes were made: 1) incubation with the detector antibody was carried out for 2 hours instead of 1 hour; 2) incubation time with the decreased amount of Strep-HRP conjugate (1:400 dilution) was 30 min at room temperature; 3) tyramide signal amplification step and incubation with Strep-HRP (FP105) were omitted. After a 30 min incubation enzymatic step of OPD oxidation, 30 µl of the reagent solution #1 (250 µM ascorbic acid in PCB), was added, and samples were irradiated as described above. The calibration curves prepared using heat-mediated ICD ELISA+PMI under the above conditions and at various times of illumination are presented in FIG. 5D. The detection limit calculated as the analyte concentration corresponding to twice the value of the background signal for the p24 antigen ICD ELISA+PMI at 8 min of illumination, is equal to 0.15 pg/mL. Thus, the analytical sensitivity of the ELISA+PAM is more than 100-fold higher than that for the assay without signal amplification. It is worth noting that the sensitivity of the heat-mediated ICD ELISA+PMI is approximately 12 times higher than that for PerkinElmer Ultrasensitive p24 assay with tyramide signal amplification.

Example 6

Preparation of the Calibration Curve for Determination of NFkB p50 Homodimer by PMI An ELISA-based kit for detection and quantification of transcription factor activation was obtained from ActiveMotif (Carlsbad, Calif.). In our studies, we used a kit for determination of NFκB p50 homodimer. This kit contains a 96-well plate to which oligonucleotide containing an NFκB consensus-binding site has been immobilized. The Jurkat (TPA+CI) nuclear extract and p50 recombinant protein are provided as positive controls for NFκB p50 activation. The activated NFκB contained in nuclear extract or p50 recombinant protein specifically bind to the oligonucleotide-coated plates. By using an antibody that is directed against either the NFkB p50 subunit, the NFκB complex bound to the oligonucleotide is detected. Addition of a secondary antibody conjugated to horseradish peroxidase (HRP) provides sensitive colorimetric readout that is easily quantified by spectrophotometry. The 96-well plate with individual strips of 8 wells is suitable for manual use or high-throughput screening applications.

The p50 NFkB ELISA-based test was performed in accordance with the manufacturer's instructions. For the p50 NFkB determination by the ELISA+PMI, the assay steps were the same as for the conventional assay procedures described above, except 1) Decreased amount of HRP-conjugated antibodies were used (see below), and 2) 100 µl of the OPD substrate solution was added to each test well instead of TMB substrate solution. After incubation, 30 µl of the reagent solution #2, containing 250 µM ascorbic acid and 1.5% Tween-20, was added, and samples were irradiated using a moderate power Device 2 for even illumination of large surfaces, moderate power defined as between 0.3 and 1 lumen/centimeter$^2$/steradian light intensity. Calibration curves for determination of p50 recombinant protein and activated cell extracts were prepared by double dilution of corresponding positive controls in buffers recommended by the manufacturer. The detection limit of the tests was estimated as the analyte concentration corresponding to twice the value of the background signal. In all experiments, the intra-assay variations did not exceed 10%. This indicates that the obtained data are reliable and reproducible.

Figure 6A:
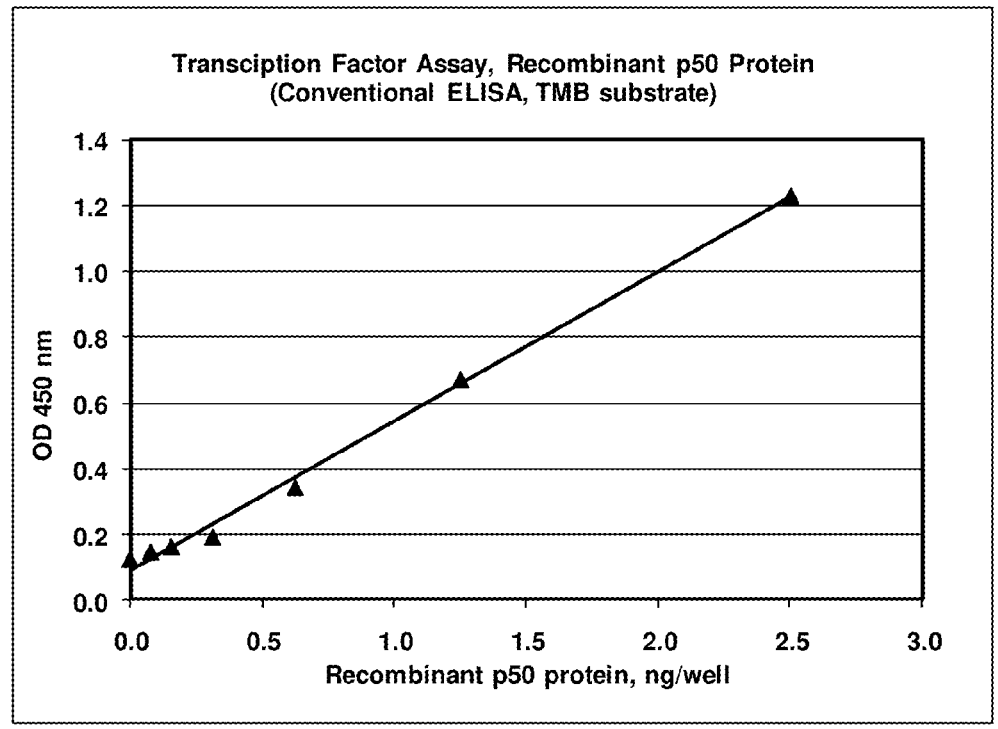
FIGS. 6A through 6D show calibration curves for determination of NFκB p50 homodimer using conventional ELISA (ActiveMotif) and p50 recombinant protein (FIG. 6A), ELISA+PMI p50 recombinant protein (FIG. 6B), conventional ELISA and nuclear extracts (FIG. 6C), and ELISA+PMI and nuclear extracts (FIG. 6D).
Figure 6B:
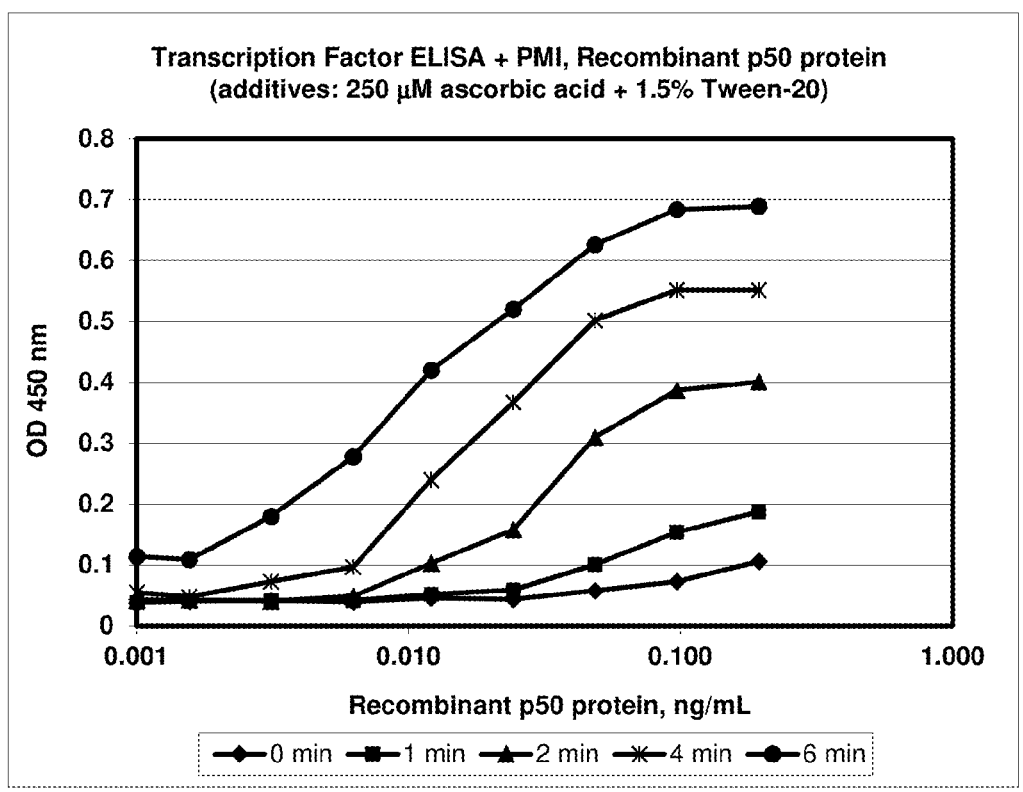

The calibration curve for quantification of p50 recombinant protein prepared using the conventional ELISA-based method is shown in FIG. 6A. The detection limit for the conventional assay is equal to approximately 0.4 ng/well. This value is in agreement with that provided by the manufacturer for the detection limit of the conventional ELISA-based test for p50 recombinant protein. The calibration curves prepared using ELISA+PMI at various times of illumination are presented in FIG. 6B. The detection limit calculated using a regression analysis for the p50 recombinant protein ELISA+PMI at 6 min of illumination, is equal to 0.005 ng/well. Thus, the analytical sensitivity of the ELISA+PMI is approximately 80-fold higher than that for the conventional assay.

Figure 6C:
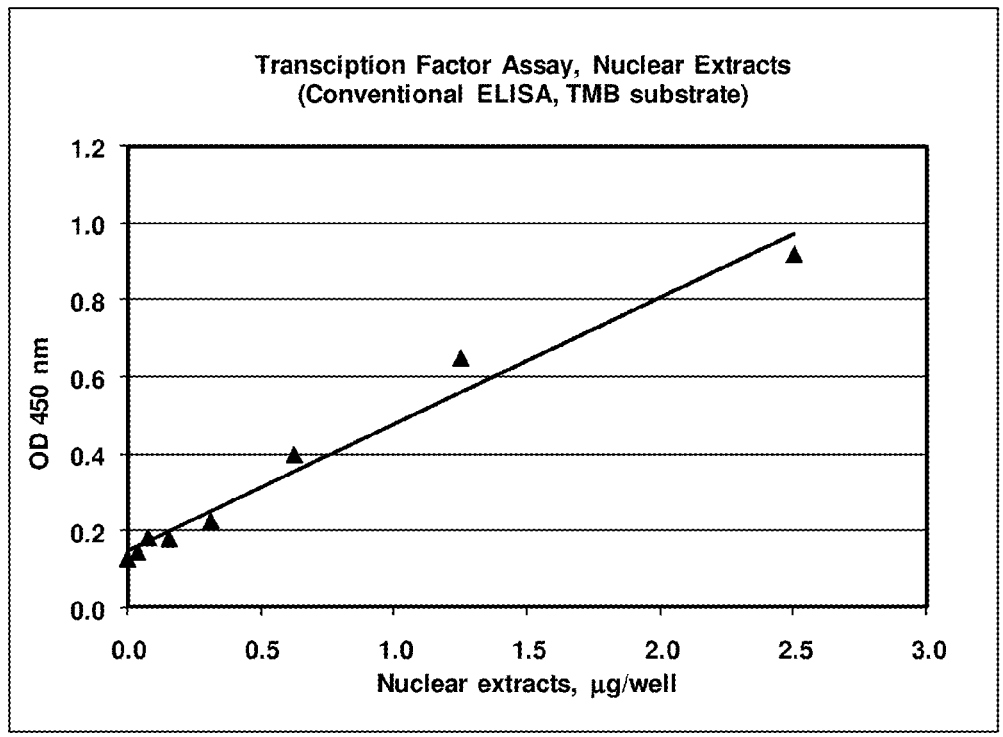
Figure 6D:
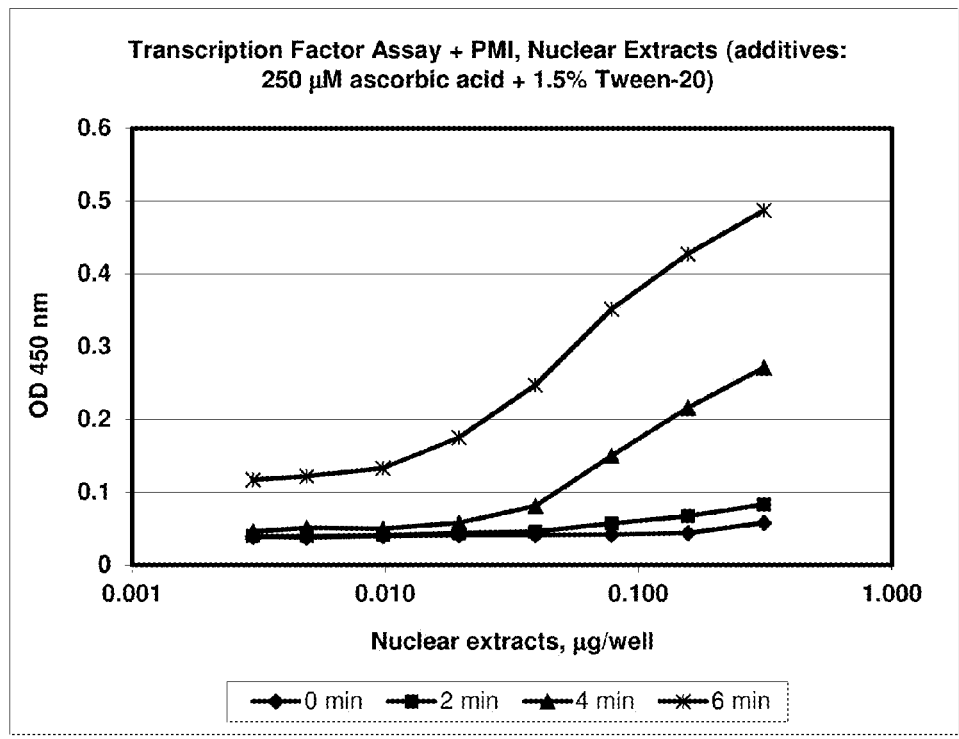

The calibration curves for determination of NFκB transcription factor in cell extracts with the NFκB p50 kit using the conventional ELISA-based test and ELISA+PMI are shown in FIGS. 6C and 6D, respectively. The detection limits calculated as described above are 0.5 µg/well and 0.03 µg/well for the conventional and ELISA+PMI tests, respectively. Thus, the sensitivity of the assay increases approximately 15-fold, as compared to that of the conventional ELISA-based test.

Example 7

The Use of the Modified PAM for Increasing of the Sensitivity of Commercially Available AMPLICOR HIV MONITOR Test, Version.1.5

Materials and Methods.
Diagnostic kit for determination of HIV load was obtained from Roche Diagnostics Corporation (Indianapolis, Ind.).
Conventional Method:
The AMPLICOR HIV-1 Monitor test, an RT-PCR with an internal quantitation standard, was performed in accordance with the manufacturer's instructions (Roche, 2003). Briefly, this test is based on five major processes: specimen preparation; reverse transcription of target RNA to generate complementary DNA (cDNA); PCR amplification of target cDNA using HIV-1 specific complementary primers: hybridization of the amplified products to oligonucleotide probes specific to the target(s); and detection of the probe bound to amplified products by colorimetric determination using HRP-avidin conjugate.

The AMPLICOR HIV-1 Monitor test permits simultaneous reverse transcription and PCR amplification of HIV-1 and HIV-1 Quantitation Standard RNA. The Master Mix reagent contains a primer pair specific for both HIV-1 and HIV-1 Quantitation Standard RNA and has been developed to yield comparable quantitation of group M subtypes of HIV-1.

The quantitation of HIV-1 viral RNA was performed using the HIV-1 Quantitation Standard. The HIV-1 Quantitation Standard is a non-infectious RNA transcript that contains the identical primer binding sites as the HIV RNA target and a unique probe binding region that allows quantitation standard amplicon to be distinguished from HIV-1 amplicon. The Quantitation Standard is incorporated into each individual specimen at a known copy number and is carried through all the aforementioned procedures along with HIV-1 target and is amplified together with the HIV-1 target. HIV-1 RNA levels in the test specimens are determined by comparing the HIV-1 signal to the Quantitation Standard signal for each specimen (see below). The Quantitation Standard compensates for effects of inhibition and controls for the amplification process to allow the accurate quantitation of HIV-1 RNA in each specimen. The stated limit of detection is 400 copies/ml and linear dynamic range is 400 to 750,000 copies/ml.

PMI Procedure:

PCR+PMI consists of two steps: conventional procedure and PMI. In PCR+PMI, the conventional method was performed without changes except the originally used TMB (tertramethylbenzidine) HRP substrate solution was replaced by the OPD substrate solution. Once the enzymatic reaction was finished, the 30 μL of the reagent solution #4 (18.6% glycerol and 1.5% Tween-20 in PCB) was added to 100 μL of the OPD substrate solution. Samples in 96-well microtiter plates were irradiated for various times using "low" power Device 3 for even illumination of large surfaces, low power defined as between 0.1 and 0.3 lumen/centimeter$^2$/steradian light intensity. Optical density of the samples was measured using a BioRad microtiter plate reader (California) at 450 nm or 492 nm after addition of stopping reagent (2M H$_2$SO$_4$).

In order to show the feasibility of using PMI for increasing of the analytical sensitivity of HIV test, a low positive control (HIV-1 L(+) control) provided with the AMPLICOR HIV-1 Monitor test kit was used. Low positive control contains non-infectious in vitro transcribed RNA (microbial) containing HIV-1 sequences in concentration from 980 to 8,900 copies/ml. In order to study the effects of dilution of low positive control before performing of PCR reaction (which models the real-life experiment with clinical samples) and the kinetics of the photochemical amplification of signals, double dilutions of low positive control at starting dilutions 1:16 and 1:64 were prepared. Since the curves prepared for low positive control at these two starting dilutions practically coincide with each other, in FIG. 7A only the ODs obtained for low positive control at starting dilution 1:64 are presented. FIG. 7B shows the results obtained for Quantitation Standard at different times of illumination.

Figure 7A:
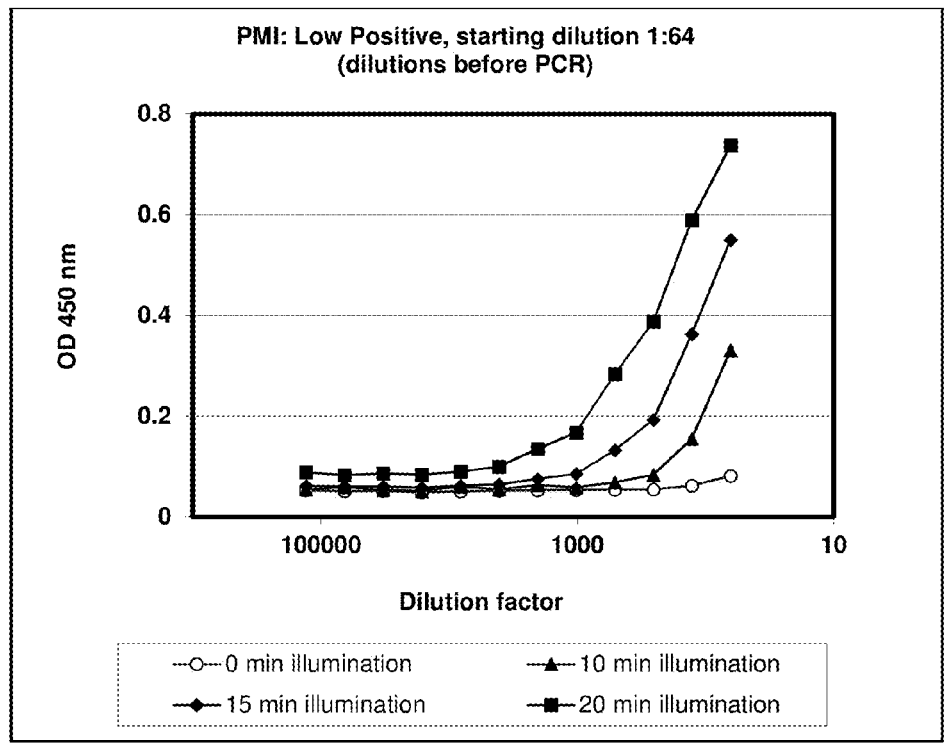
Figure 7B:
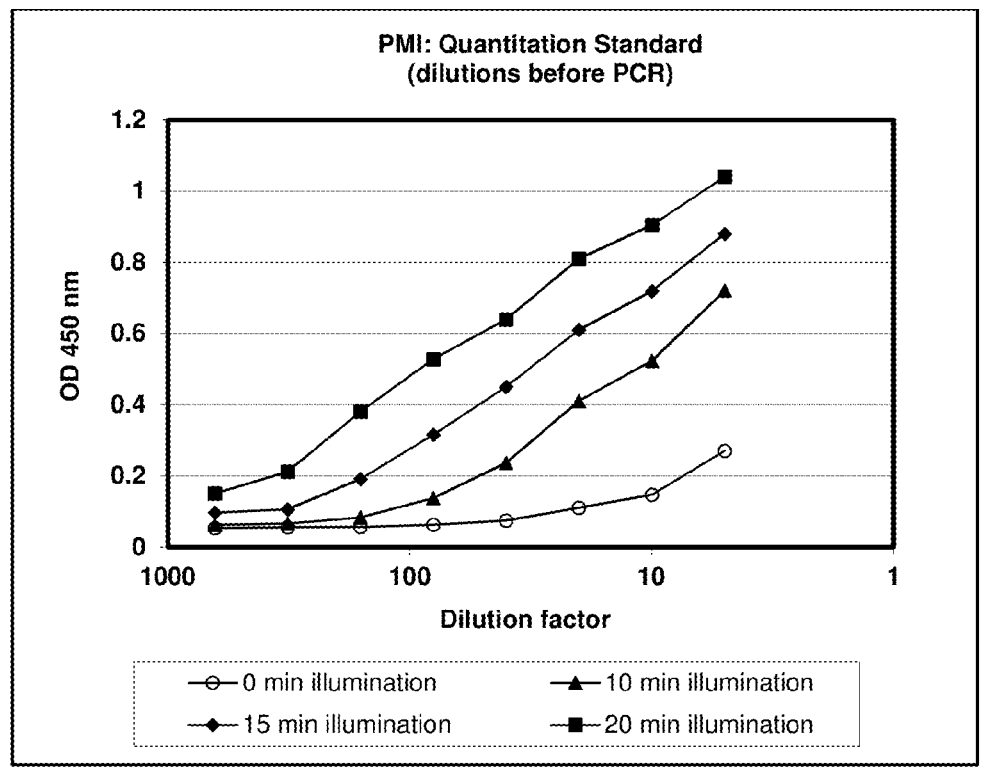

As can be seen in FIG. 7A, the detection limit of PCR+PMI is approximately 1:512 dilution of the low positive control. The detection limit of the conventional assay in this experiment was determined to be a 1:25 dilution of the low positive control. Results demonstrate that the limit of detection for HIV using PCR+PMI can be decreased at least 20-fold as compared to the conventional method. As can be seen in FIG. 7B, ODs of the quantitation standard is changing with illumination and have to be taken into consideration when calculating HIV-1 viral load (see below).

In order to examine the possibility of using PCR+PMI for quantitative determination of HIV load in clinical samples, values of HIV load in low positive control and several clinical samples by the conventional method and by PCR+PMI we calculated, and the obtained results were compared.

The AMPLICOR HIV-1 RNA MONITOR Test v.1.5 quantitates viral load by utilizing a second target sequence (HIV-1 Quantitation Standard (QS)) that is added to the amplification specimen at a known concentration. The QS is a non-infectious 233 nucleotide in vitro transcribed RNA molecule with primer binding region identical to those of the HIV-1 target sequence. The QS, therefore, contains SK145 and SKCC1B primer binding sites and generates a product of the same length (155 bases) and base composition as the HIV-1 target. The probe-binding region of the QS was modified to differentiate QS-specific amplicon from HIV-1 target amplicon.

In the linear range of the assay, the optical density in each well of the plate is proportional to the amount of HIV-1 or QS amplicon in the well. Total OD is calculated by multiplying the OD in each well by the dilution factor for that well. The calculated total HIV-1 OD or total QS OD is proportional to the amount of HIV-1 or QS RNA, respectively, present in each reverse transcription/PCR amplification reaction. The amount HIV-1 RNA in each specimen is calculated from the ratio of the total optical density for the HIV-1 specific well to the total optical density for the QS-specific well and the input number of QS RNA molecules using the following equation:

$$\left[\frac{\text{Total } HIV\text{-}1 \ OD}{\text{Total } QS \ OD}\right] \times \text{Input } QS \text{ copies per } PCR \text{ reaction} \times$$

Sample volume factor = $HIV\text{-}1$ RNA copies/ml where Total HIV-1 OD is the calculated Total OD for HIV-1 amplicon, Total QS OD is the calculated Total OD for HIV-1 QS amplicon, Input QS copies per PCR reaction is the number of copies of QS in each reaction; this information is lot-specific, Sample volume factor is the factor to convert copies/PCR to copies/ml, and usually equals 40.

In more detail, the specimens in neat and 1:5, 1:25, 1:125, 1:625 and 1:3125 serial dilutions are added to the wells from A to F containing a complementary oligonucleotide to HIV-1 amplicon. The specimens in neat and 1:5 dilutions are added to wells G and H containing a complementary oligonucleotide to QS amplicon. Every plate contains a negative control (negative human plasma). Then, the HIV-1 OD above and closest to 0.2, and QS OD above and closest to 0.3 are selected for the further calculation: The total HIV-1 OD and total QS OD are calculated by multiplying the background-corrected OD value (OD (sample or QS)–OD (negative control)) by the dilution factor associated with that well, and the above formula is used for the calculation of HIV-1 load.

The incorporation of QS to each specimen is a necessary step in order to mitigate the variations in the performance of several test procedures. It should be noted that the above original approach for the calculation of HIV load has certain drawbacks. Indeed, the requirement for selecting of HIV and QS ODs above and closest to 0.2 and 0.3, respectively, is caused by the fact that the kinetics of enzyme-catalyzed increase of the signals is not linear, and as a consequence the final ODs are not proportional to the initial concentration of the analytes (amplicons). Since only two concentrations of QS are used in the assay, the selected ODs could differ significantly from each other, and due to non-linearity of the signal increase, the errors in the calculation of HIV load could be considerable.

The HIV and QS OD values closest to each other and above OD=0.2 were selected for the further HIV load calculation. In this case, variations caused by the non-linear signal increase of enzymatic reaction and photoamplification will be minimized. Initially, in PCR+PMI the above original protocol for calculations of HIV load was used. However, more accurate values of HIV-1 load can be obtained using a slightly modified protocol. The following example illustrates the suggested approach.

Three clinical samples containing HIV virus in different concentrations were used. Conventional and PCR+PMI were performed, and HIV-1 load using the above original and modified protocols have been calculated. In order to compare the results obtained using the conventional method and PCR+PMI, samples containing HIV virus in concentrations that could be detected by the conventional procedure were used. In PCR+PMI, however, we diluted samples in negative human plasma until the level when HIV load was undetectable by the conventional test, that is samples PS, TJS and CAP-5-05 were used at starting dilutions 1:200, 1:400 and 1:100, respectively. PCR+PMI was performed without any changes in the conventional procedure, except in PCR+PMI, dilutions of quantitation standard were 1:10 and 1:50 whereas in the conventional method they were 1:1 and 1:5.

Figure 7C:
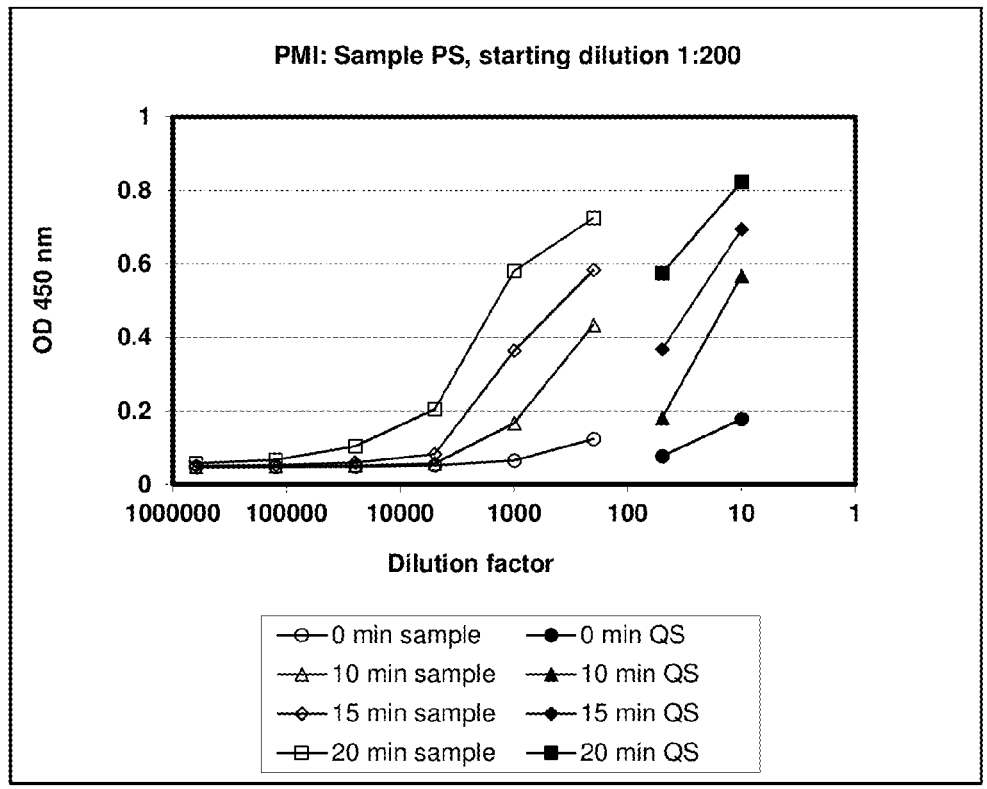

In FIG. 7C, the results obtained for clinical sample PS at starting dilution 1:200 are presented. As can be seen in this Figure, the ODs obtained for PS and QS are increasing with increasing the illumination time. The similar graphs were obtained for other clinical samples. Using the data from these graphs, HIV load in these specimens at different times of illumination using a modified protocol was calculated. The results are summarized in FIG. 7D. For each sample the values of HIV load calculated at different times of illumination are practically the same, and the coefficient of variation does not exceed 10%. These results show that HIV load determination does not depend on illumination time. Note that in the photoamplification method, it is impossible to use the original protocol for the calculation of HIV load due to the fact that the calculated values of HIV load depend significantly on illumination time. Therefore, in PCR+PMI only the modified protocol for the calculation of HIV load was used. It should also be noted that different lots of Low positive samples having different viral loads were used for obtaining the results presented in FIGS. 7A and 7D.

FIG. 7E summarizes the average values of HIV loads (and corresponding coefficients of variation) for low positive control and clinical samples obtained at different starting dilutions of samples and different days. Results demonstrate that there is a good agreement with the results obtained by the conventional method and PCR+PMI. The coefficients of variation are rather high for both conventional and PCR+PMI. This is not unusual because according to a much more detailed study carried out by the manufacturer of this kit, coefficients of variation in the linear range for this kit were between 30 and 94%. It should be emphasized that for the conventional method there is no significant difference between the values of HIV load and coefficients of variation calculated using the original and modified protocols. Therefore, both protocols are valid for the calculation of HIV load in the samples.

Example 8

The Use of OPD as an Insoluble HRP Substrate in Membrane-Based Assay (Blotting Analysis)

1. Comparison of Insoluble Substrates for HRP-Mediated Membrane Assays

Chloronaphtol (4-CN), 3-aminoethylcarbazol (AEC), HRP-conjugated goat antihuman antibodies and polyclonal human antibodies were purchased from Sigma. TMB soluble and insoluble substrate solutions were obtained from Transgenic Sciences, Inc (Massachusettes) and Calbiochem-Novabiochem Corp. (La Jolla, Calif.), respectively. Tablets containing 12.8 mg orthophenylenediamine dihydrochloride were purchased from Abbott Laboratories (North Chicago, Ill.). Nitrocellulose membranes with 0.45 µm pores and Nylon membranes "Hybond" were obtained from GE Healthcare Life Sciences (Piscataway, N.J.). To prepare the OPD substrate solution, a tablet containing 12.8 mg OPD (Abbott) was dissolved in 10 mL of 0.1M phosphate-citrate buffer, pH 5.0 containing 0.01% hydrogen peroxide. 4-CN and AEC substrate solutions were prepared according to standard previously published procedures (Jackson and Blythe, 1993). Commercially available insoluble TMB substrate solution (Calbiochem-Novabiochem) was used as received.

Figures 8A, 8B:
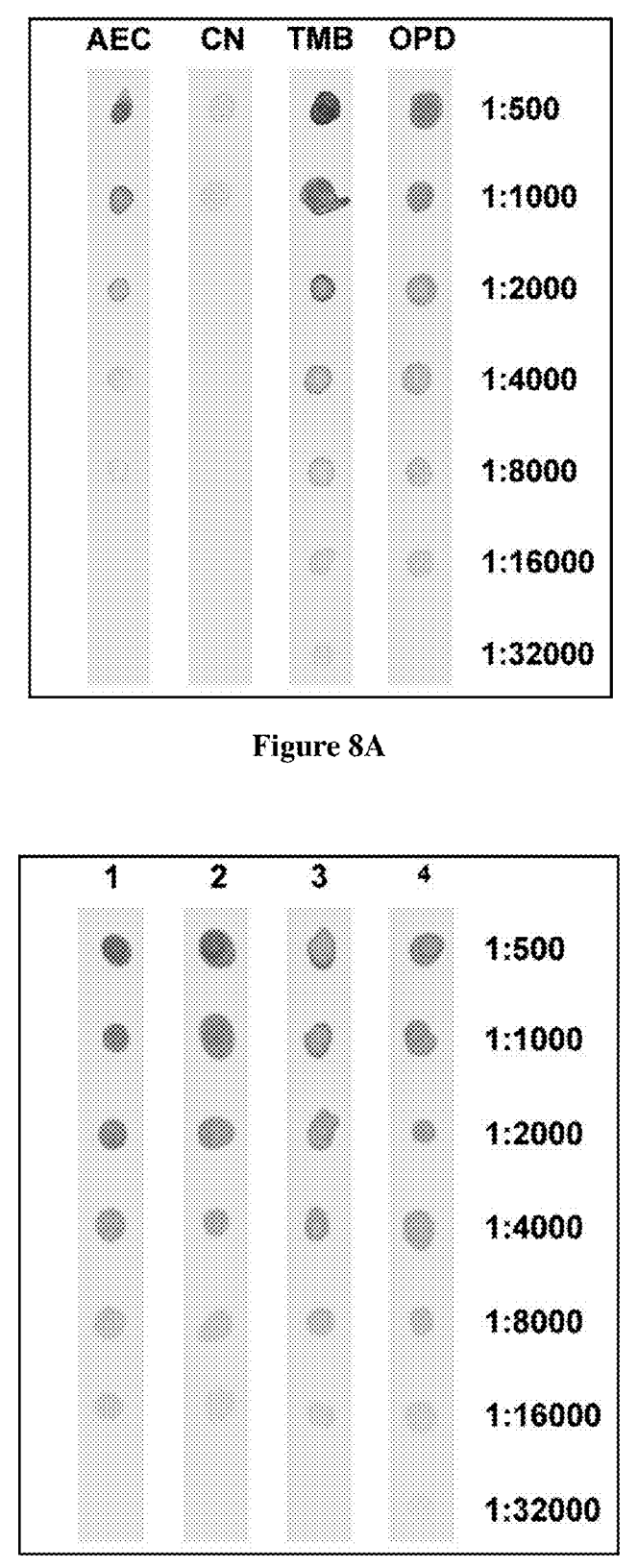

To show the possibility of using OPD as an insoluble HRP substrate in membrane-based (blotting) analysis and compare the efficacy of different HRP insoluble substrates, serial double dilutions of HRP-conjugated antibodies were made in 0.01M phosphate buffered saline (PBS), pH 7.2. Two µl aliquots were spotted on the nitrocellulose or nylon membrane strips. The membrane strips were air-dried and then immersed for 30 minutes in freshly made up chromogenic substrate solutions in their appropriate buffers. The strips were then removed from the chromogenic substrate solutions, washed five times with distilled water, air-dried and photographed. Representative results using 4-CN, AEC, TMB and OPD as substrates for HRP on nitrocellulose membrane are shown in FIG. 8A. As can be seen in this Figure, the detection system using OPD as an HRP substrate is more sensitive than systems using 4-CN and AEC and offers sensitivity comparable to that of the system employing a commercial TMB insoluble substrate solution. Practically the same results for were obtained using "Hybond" nylon filters (see FIG. 8B, strip 2).

FIG. 8B demonstrates that blocking of nitrocellulose or nylon membrane strips with 5% BSA after spotting a various amounts of HRP-conjugated antibodies does not prevent the OPD oxidation product to be adsorbed onto the strips surface. OPD was added to the strips 1 (nitrocellulose) and 2 (nylon) without blocking the membranes with BSA. Strips 3 (nitrocellulose) and 4 (nylon) were blocked with 5% BSA after spotting various amounts of HRP-conjugated antibodies. As can be seen in FIG. 8B, the assay sensitivities with OPD for the strips unblocked and blocked with BSA are between 16,000-32,000 dilution of the stock HRP-conjugate solution.

2. Application of the PMI Method to Membrane- and Histochemistry-Based Assays

Figure 8C:
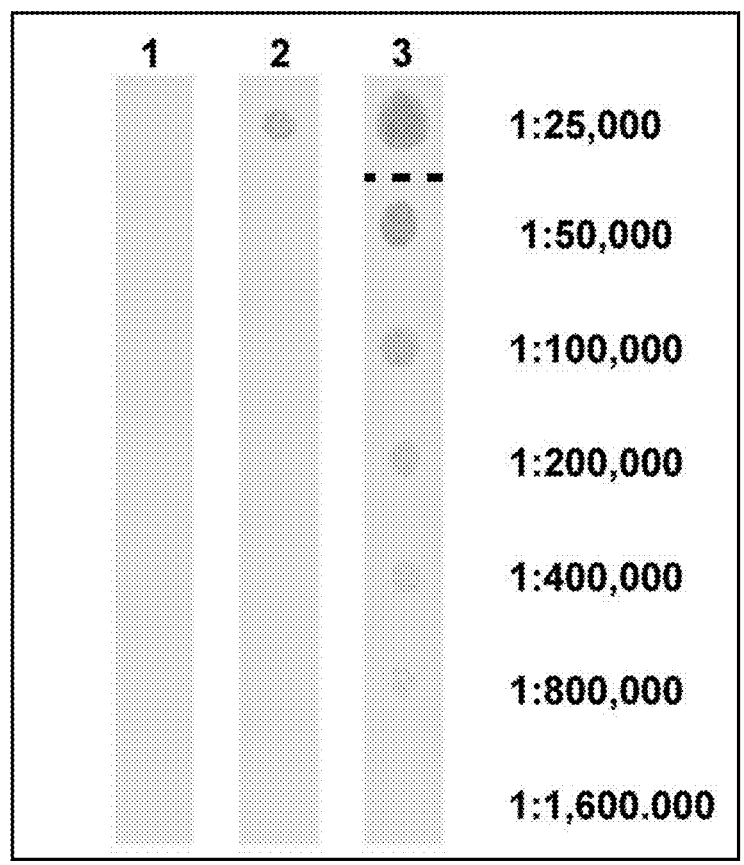

In order to show the possibility of using the Photochemical Method of the present invention (PMI) for membrane-based assays, serial dilutions of HRP-conjugated antibodies were prepared in 0.01M phosphate buffered saline (PBS), pH 7.2. Two µl aliquots were spotted on the nylon membrane strips. The membrane strips were air-dried and then immersed for 30 minutes in freshly made up OPD chromogenic substrate solution described above. The strips were then removed from the chromogenic substrate solution, washed five times with distilled water. Then, the strips were immersed into OPD substrate solution containing 250 µM ascorbic acid and 1.5% Tween 20 for 5 min. After this, they were taken off the solution and without washing placed on the glass surface. Then, they were illuminated for 5 min from above using the device for even illumination of large surfaces. The results are shown in FIG. 8C. As can be seen in FIG. 8C, the sensitivity of the assay plus PMI is approximately 1:800,000 dilution of the stock HRP solution, which is approximately 30-fold higher than that for the conventional procedure with no PMI (~1:25,000).

Examples 9-11

The procedure of Example 2 was repeated except that ascorbic acid or ascorbic acid+1.5% Tween 20 was replaced by the following additives:

Example 9

1 mM or 0.5 mM L-Ascorbic acid acetonide or 1 mM or 0.5 mM L-Ascorbic acid acetonide+1.5% Tween 20;

Example 10

1 mM or 0.5 mM L-Ascorbyl octanoate or 1 mM or 0.5 mM L-Ascorbyl octanoate
+1.5% Tween 20;

Example 11

1 mM or 0.5 mM L-Ascorbyl dodecanoate or 1 mM or 0.5 mM L-Ascorbyl dodecanoate+1.5% Tween 20.

The increase in the analytical sensitivity of the assays for determination of HRP (catalyzing the photosensitizer DAP) in aqueous solution using various additives was calculated and shown to have been increased from about 50- to about 100-fold as compared with conventional procedure.

Example 12

The procedure of Example 1 was repeated except that the photosensitizer DAP was replaced by a photosensitizer Eosin Y (starting concentration is 10 µM) and 100 µM, 50 µM, 20 µM and 10 µM sodium ascorbate was used as an additive. The improvement in signal/background ratio was measured and shown to be from about 3- to about 5-fold at 100 µM sodium ascorbate as compared to when no additive was used.

Example 13

The procedure of Example 1 was repeated except that photosensitizer DAP was replaced by photosensitizer Eosin Y (starting concentration is 10 µM), substrate OPD was replaced with the substrate TMB and 50 µM, 20 µM and 10 µM sodium ascorbate was used as an additive. The improvement in signal/background ratio was measured and it is equal to from 2- to 3-fold at 50 µM sodium ascorbate as compared to when no additive was used.

REFERENCES CITED

Arababadi, M. K., Hassanshahi, G., Pourfathollah, A. A., Zarandi, E. R. and Kennedy, D. (2011) Post-Transfusion Occult Hepatitis B (OBI): A Global Challenge for Blood Recipients and Health Authorities. Hepat Mon 11, 714-8.

Avrameas, S, and Uriel, J. (1966) [Method of antigen and antibody labelling with enzymes and its immunodiffusion application]. C R Acad Sci Hebd Seances Acad Sci D 262, 2543-5.

Bystryak, S. (1998) U.S. Pat. No. 5,776,703. Immunoassay.

Bystryak, S., Goldiner, I., Niv, A., Nasser, A. M. and Goldstein, L. (1995) A homogeneous immunofluorescence assay based on dye-sensitized photobleaching. Anal Biochem 225, 127-34.

Catty, D. (1989) Antibodies: A Practical Approach, Vol. II. Oxford University Press, Oxford. CDC. Bioterrorism Agents/Diseases. In, Vol. 2013.

Edberg, S. C. (1985) Principles of nucleic acid hybridization and comparison with monoclonal antibody technology for the diagnosis of infectious diseases. Yale J Biol Med 58, 425-42.

Eglen, R. M., Reisine, T., Roby, P., Rouleau, N., Illy, C., Bosse, R. and Bielefeld, M. (2008) The use of AlphaScreen technology in HTS: current status. Curr Chem Genomics 1, 2-10.

Fleming, G. R., Knight, W. E. A., Morris, J. M., Morrison, R. J. S, and Robinson, G. W. (1977) Picosecond fluorescence studies of xanthene dyes. J Am Chem Soc 99, 4306-4311.

Gandin, E., Lion, Y. and Van de Vorst, A. (1983) Quantum yield of singlet oxygen production by xanthene derivatives. Photochem Photobiol 37, 271-278.

Ivnitski, D., Abdel-Hamid, I., Atanasov, P. and Wilkins, E. (1999) Biosensors for detection of pathogenic bacteria. Biosensors & Bioelectronics 14, 599-624.

Jackson, P. and Blythe, D. (1993) Immunocytochemistry: Practical Approach. Oxford University Press, Oxford.

Mazenko, R. S., Rieders, F. and Brewster, J. D. (1999) Filtration capture immunoassay for bacteria: optimization and potential for urinalysis. J Microbiol Methods 36, 157-65.

Meng, J. H., Zhao, S. H., Doyle, M. P. and Kresovich, S. (1996) Polymerase chain-reaction for detecting E. coli 1157:H7. Intl J Food Microbiol 32, 103-113.

Motsenbocker, M., Masuya, H., Shimazu, H., Miyawaki, T., Ichimori, Y. and Sugawara, T. (1993a) Photoactive methylene blue dye derivatives suitable for coupling to protein. Photochem Photobiol 58, 648-652.

Motsenbocker, M., Sugawara, T., Shintani, M., Masuya, H., Ichimori, Y. and Kondo, K. (1993b) Establishment of the optically pumped chemiluminescence technique for diagnostics. Anal Chem 65, 403-408.

Nakane, P. K. and Pierce, G. B., Jr. (1966) Enzyme-labeled antibodies: preparation and application for the localization of antigens. J Histochem Cytochem 14, 929-31.

Roche. (2003) AMPLICOR HIV-1-MONITOR test package insert. Roche Diagnostic Systems, Branchburg, N.J.

Sandell, J. H. and Masland, R. H. (1988) Photoconversion of some fluorescent markers to a diaminobenzidine product. J Histochem Cytochem 36, 555-9.

Sawke, N. G. and Sawke, G. (2010) Preventing Post-Transfusion Hepatitis by screening blood donors for IgM Antibody to Hepatitis B core antigen. J Glob Infect Dis 2, 246-7.

Schmidt, R. (2006a) Comment on "Quenching mechanism of rose bengal triplet state involved in photosensitization of oxygen in ethylene glycol". Journal of Physical Chemistry A 110, 7749-7749.

Schmidt, R. (2006b) Photosensitized generation of singlet oxygen. Photochemistry and Photobiology 82, 1161-1177.

Sperveslage, J., Stackebrandt, E., Lembke, F. W. and Koch, C. (1996) Detection of bacterial contamination, including bacillus spores, in dry growth media and in milk by identification of their 16S RDNA by polymerase chain-reaction. J Microbiol Methods 26, 219-224.

Timoshenko, V. (2009) SINGLET OXYGEN GENERATION AND DETECTION FOR BIOMEDICAL APPLICATIONS. In: M.I. Baraton (Ed) Sensors for Environment, Health and Security, Vol. II, NATO Science for Peace and Security Series C p. 295-309.

Ullman, E. F., Kirakossian, H., Singh, S., Wu, Z. P., Irvin, B. R., Pease, J. S., Switchenko, A. C., Irvine, J. D., Dafforn, A., Skold, C. N. and et al. (1994) Luminescent oxygen channeling immunoassay: measurement of particle binding kinetics by chemiluminescence. Proc Natl Acad Sci USA 91, 5426-30.

Yu, H. and Bruno, J. G. (1996) Immunomagnetic-electrochemiluminescent detection of Escherichia coli O157 and Salmonella typhimurium in foods and environmental water samples. Appl Environ Microbiol 62, 587-92.

What is claimed is:

1. An assay for detecting an analyte in a fluid sample, the assay comprising the steps of:
    a) binding the analyte to a first entity having an affinity to the analyte, said entity labeled with a photosensitizer or an enzyme to catalyze producing of said photosensitizer, b) adding to a mixture of said analyte and said entity a substrate for a photochemical reaction, said substrate is capable to be converted to a product of the photochemical reaction when said mixture of said entity, said analyte and said substrate is irradiated with a light at a wavelength within a light absorption spectrum of said photosensitizer, c) adding a reagent solution containing an additive described by formula (1)

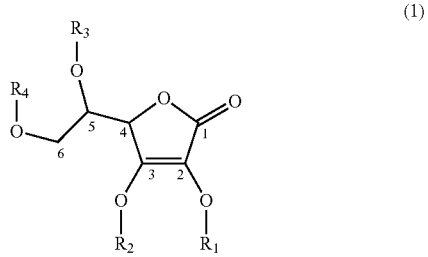

(1)

wherein said additive is an ascorbic acid or a derivative thereof obtained by at least one substitution at position 2, position 3, position 5, position 6 or any combinations thereof with at least one group of atoms selected from a group consisting of an anion group of atoms, an aliphatic group of atoms not exceeding 16 carbon atoms, and an aromatic group of atoms not exceeding 16 carbon atoms;

d) conducting the photochemical reaction by irradiating the mixture of step (c) with said light, and e) detecting the analyte by measuring an optical signal corresponding to the amount of the product of the photochemical reaction.

2. The assay as in claim 1, wherein said optical signal is selected from a group consisting of an optical density, reflectance, fluorescence, chemiluminescence and electrochemiluminescence of said product of the photochemical reaction.

3. The assay of claim 1, wherein the photosensitizer is selected from a group consisting of a phenazine, a phenazine derivative, a 2,3-diamino-phenazine, an eosin, an eosin derivative, an erythrosine, an erythrosine derivative, a toluidine blue, a merocyanine 540, Rose Bengal, a methylene blue, a porphyrine, a hematoporphyrin, a porphyrine derivative, a phthalocyanine, a phthalocyanine derivative, an aluminum phthalocyanine tetrasulfonate (AlPCS) derivative, a riboflavin, and a quantum dot.

4. The assay of claim 1, wherein the enzyme is selected from a group consisting of a horseradish peroxidase, an alkaline phosphatase, a β-galactosidase, and their biotin-streptavidin complexes.

5. The assay of claim 1, wherein the substrate is selected from a group consisting of a phenylenediamine, a phenylenediamine derivative, a benzidine or a derivative thereof, a diaminobenzidine, 3,3',5,5'-Tetramethylbenzidine, a olefin or a derivative thereof, a luminol or a derivative thereof, a dioxetane or a derivative thereof, a benzofurane or a derivative thereof, tyramine-biotin, and tyramine-photosensitizer.

6. The assay as in claim 1, wherein said substrate or said photosensitizer is embedded in microparticles, nanoparticles or liposomes.

7. The assay of claim 1, wherein the analyte is present at a cell surface, a nitrocellulose or a nylon membrane; the entity having an affinity to the analyte is an antibody against the analyte or a complex of primary and secondary antibodies labeled with the photosensitizer or the enzyme to catalyze producing thereof, wherein the substrate is selected from a group including a phenylenediamine derivative, a benzidine derivative, a tyramine-biotin, and a tyramine-photosensitizer.

8. The assay of claim 1, wherein said step (a) further comprises adding a second entity with an affinity to the analyte, wherein said analyte binds to said first entity and said second entity.

9. The assay as in claim 8, wherein said first entity is attached to a solid support embedding the photosensitizer and said second entity is attached to a solid support embedding the substrate.

10. The assay of claim 8, wherein all steps are carried out in a single mixture of all solutions without physical separation of bound and unbound fractions of all reagents.

11. The assay of claim 8, wherein the assay is an ELISA-assay or a PCR-based assay, the first entity or the second entity is an antibody or a oligonucleotide, the enzyme to catalyze producing the photosensitizer is a horseradish peroxidase or biotin-streptavidin-horseradish peroxidase complex; the substrate is an orthophenylenediamine.

12. The assay of claim 1, wherein the analyte is selected from a group consisting of a *Clostridium difficile* toxin A, a *Clostridium difficile* toxin B, a rotavirus, a Hepatitis B surface antigen, an HIV p24 antigen, a p50 recombinant protein NFkB p50 homodimer, an RNA, a DNA, an mRNA, an cDNA, a prostatic specific antigen (PSA), an Anthrax (*Bacillus anthracis*), an Arenaviruse, a *Clostridium botulinum* toxin, a *Brucella* specie, a *Burkholderia pseudomallei*, a *Chlamydia psittaci*, a *Vibrio cholerae*, an Ebola virus, an *Escherichia coli* O157:H7, a variola major, a Staphylococcal enterotoxin B, a *Francisella tularensis*, a *Salmonella*, a *Rickettsia prowazekii*, a *Yersinia pestis*, a *Cryptosporidium parvum*, and *Shigella*.

13. The assay of claim 1, wherein said additive in step (c) is an ascorbic acid or a derivative thereof obtained by at least one substitution at position 5, position 6 or both position 5 and position 6 with at least one group of atoms selected from a group consisting of an anion group of atoms, an aliphatic group of atoms not exceeding 16 carbon atoms, and an aromatic group of atoms not exceeding 16 carbon atoms.

14. The assay of claim 1, wherein said additive in step (c) is an O-alkyl ascorbic acid derivative comprising said at least one substitution of R3 at position 5, R4 at position 6, or both R3 at position 5 and R4 at position 6 by a group of $(CH_2)_x$-$CH_3$, where x is not to exceed 14.

* * * * *